United States Patent [19]
Glazer et al.

[11] Patent Number: 5,929,227
[45] Date of Patent: Jul. 27, 1999

[54] DIMERIC FLUORESCENT ENERGY TRANSFER DYES COMPRISING ASYMMETRIC CYANINE AZOLE-INDOLENINE CHROMOPHORES

[75] Inventors: Alexander N. Glazer, Orinda; Scott C. Benson, Oakland, both of Calif.

[73] Assignee: The Regents of the University of California, Berkeley, Calif.

[21] Appl. No.: 08/965,913

[22] Filed: Nov. 7, 1997

Related U.S. Application Data

[62] Division of application No. 08/500,798, Jul. 12, 1995, Pat. No. 5,760,201.

[51] Int. Cl.[6] .............................. C07H 21/02; C07H 21/04
[52] U.S. Cl. ........................................... 536/26.6; 536/22.1
[58] Field of Search ............................. 435/6; 536/25.32, 536/26.6, 22.1

[56] References Cited

U.S. PATENT DOCUMENTS

| | | | |
|---|---|---|---|
| 5,312,921 | 5/1994 | Glazer et al. | 536/52.32 |
| 5,564,554 | 10/1996 | Glazer | 536/26.6 |
| 5,565,554 | 10/1996 | Glazer et al. | 536/26.6 |
| 5,646,264 | 7/1997 | Glazer | 536/25.32 |
| 5,760,201 | 6/1998 | Glazer | 536/22.1 |

OTHER PUBLICATIONS

Benson, et al., *Nucleic Acids Research* (1993) vol. 21:5720–5726.

Hamer, "The Cyanine Dyes in Related Compounds," *The Chemistry of Heterocyclic Compounds* (1964) vol. 18:210–239.

Ernst, et al., *Cytometry* (1989) vol. 10:3–10.

*Primary Examiner*—Eggerton A. Campbell
*Attorney, Agent, or Firm*—Bret Field; Bozicevic, Field & Francis

[57] ABSTRACT

Novel fluorescent heterodimeric DNA-staining energy transfer dyes are provided combining asymmetric cyanine azole-indolenine dyes, which provide for strong DNA affinity, large Stokes shifts and emission in the red region of the spectrum. The dyes find particular application in gel electrophoresis and for labels which may be bound to a variety of compositions in a variety of contexts. Kits and individual compounds are provided, where the kits find use for simultaneous detection of a variety of moieties, particularly using a single narrow wavelength irradiation source. The individual compounds are characterized by high donor quenching and high affinity to dsDNA as a result of optimizing the length of the linking group separating the two chromophores.

10 Claims, 14 Drawing Sheets

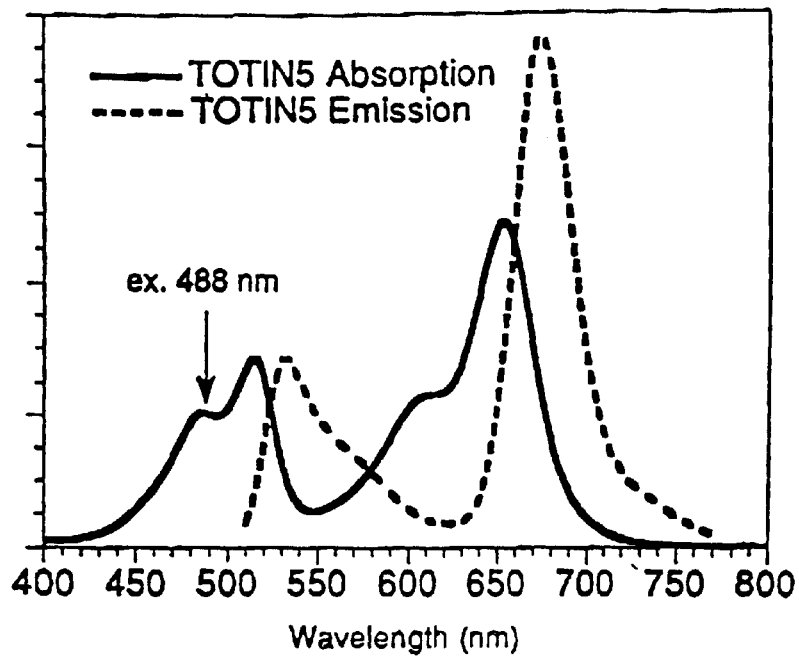
Fig. 3A
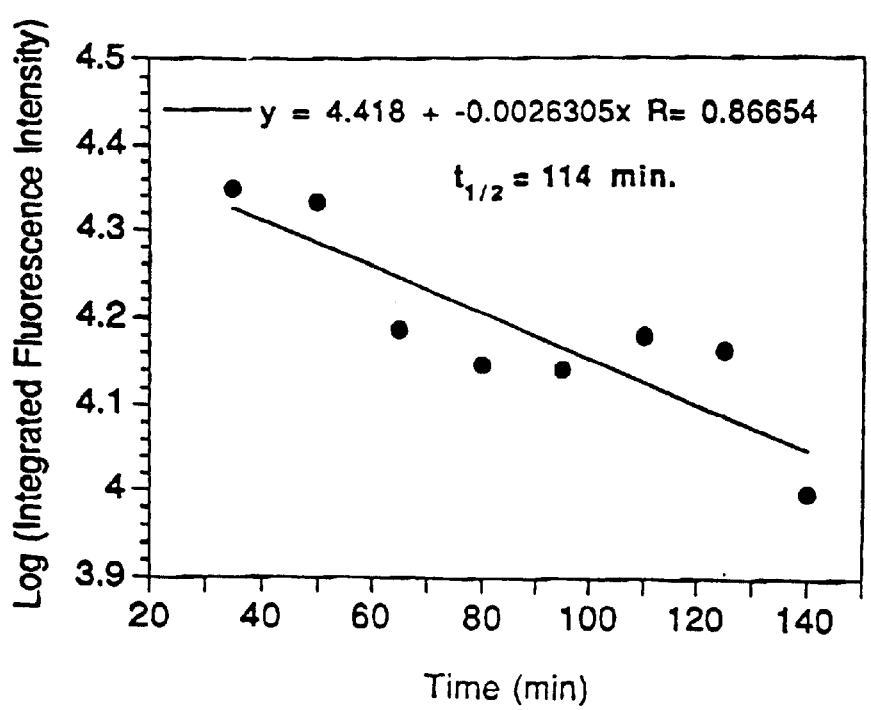
Fig. 3B
FIG. 3

3

R = CH₃, C₃H₆I, C₄H₈I, C₅H₁₀I

9  X = C(CH₃)₂
11 X = S

10 X = S
12 X = C(CH₃)₂

13

14

15

R =

TOTAB
18a (n = 3)
18b (n = 4)
18c (n = 5)
18d (n = 6)

TOSTAB
19 (n = 3)

TOTAG
20 (n = 3)

Scheme 3

Scheme 4

13A

13B 5,929,227

DIMERIC FLUORESCENT ENERGY TRANSFER DYES COMPRISING ASYMMETRIC CYANINE AZOLE-INDOLENINE CHROMOPHORES

CROSS-REFERENCE TO RELATED APPLICATIONS

This is a divisional of application Ser. No. 08/500,798 filed Jul. 12, 1995, now U.S. Pat. No. 5,760,201.

INTRODUCTION

Technical Field

The field of this invention is DNA fluorescent stains.

Background

Detection of fluorescent signals finds wide applications in a variety of situations and under a variety of conditions. Fluorescence has many advantages as a means of generating a detectable signal. Fluorescence does not suffer from the many disadvantages of a radioactive label, while in many cases it provides for a high level of sensitivity.

There is substantial interest in being able to obtain fluorescence at longer wavelengths, where there is less interference from light resulting from scattering from components in the medium being irradiated. By providing for combinations of dyes with large Stokes shifts, one can achieve high sensitivity fluorescence detection of DNA, where the dye becomes bound to DNA and provides for a shift in the spectral properties of the resulting dimer.

Relevant Literature

Co-pending applications, Ser. Nos. 08/161,231; 08/009,704; 08/060,910; and 08/189,924 describe monomeric and dimeric dyes for binding to DNA finding application in gel electrophoresis and as labels in a variety of contexts. U.S. Pat. No. 5,312,921 provides for a number of different homodimeric and heterodimeric dyes which bind to DNA. The stability of dsDNA-dye complexes is described by Benson et al. (1993) *Nucleic Acids Res.* 21, 5720–5726. Carbocyanine dyes are described by Hammer, "The Cyanine Dyes in Related Compounds," in *The Chemistry of Heterocyclic Compounds*, Vol. 18, pages 210 and 239, Interscience Publishers, NY, 1964. Synthesis and application of cyanine dyes for use as covalent labels are described in Ernst et al., (1989) *Cytometry* 10,3–10 and Mujumdar et al., (1989) *Cytometry*, 10, 11–19.

BRIEF DESCRIPTION OF THE FIGURES

FIG. 3A illustrates the absorption and fluorescence emission spectra of TOTIN-5 (17a);

FIG. 3B is a graph of the rate of dissociation of preformed λDNA/HindIII-TOTIN-5 (17a) complexes during electrophoresis.

SUMMARY OF THE INVENTION

Figure 1:
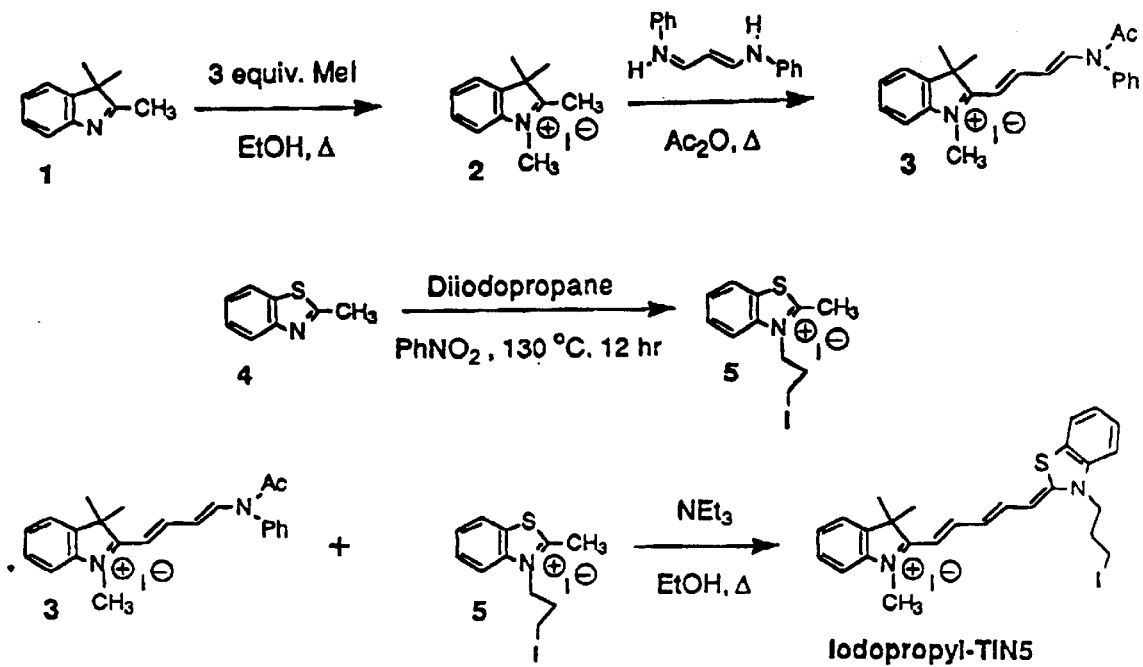
FIG. 1 (Scheme 1) is the synthetic scheme for the preparation of N-iodopropyl-TIN-5 2-[5'-(3"iodopropyl-(benzo-1", 3"-thiazole)-2"-ylidene)-1',3'-pentadienyl]-methyl-3,3-dimethylindoleninium iodide.

Novel heterodimeric fluorescent asymmetric carbocyanine dyes are provided for binding to DNA to serve as fluorescent stains. The dyes have a strong affinity for DNA and can be used in gel electrophoresis for extended periods of time, even with small DNA molecules. The dyes provide for absorption at convenient wavelengths below about 500 nm ($\epsilon$>40,000) with strong emission at wavelengths above 650 nm to substantially diminish background, as well as contributions from dyes emitting at shorter wavelengths where two or more dyes are used in multiplex applications. Enhancement of at least one of the affinity for DNA in gel electrophoresis and the quenching of donor fluorescence is obtained by varying the length of the linker bridging the two dye chromophores in the heterodimer.

DESCRIPTION OF SPECIFIC EMBODIMENTS

Novel compositions and their use are provided, where the compositions comprise fluorescent asymmetric dicarbocyanine azole-indolenine dyes, their complexes with DNA, and their use in gel electrophoresis and as labels for labeling a wide variety of materials in various contexts.

The subject dyes may be divided into three parts: the carbocyanine azole dye, the carbocyanine azole-indolenine dye; and the linking group. The asymmetric carbocyanine azole dyes have been extensively described in the literature, as well as their preparation. The cyanine dye structures contain two end groups with a positive charge in conjugation through a linking methine chain, the asymmetric cyanine dyes are unique in having two different groups. The linking methine chain may contain from about 1 to 9 carbon atoms in the chain and may be part of an alicyclic or aromatic ring, and may be substituted with alkyl or heteroatom functional groups. The asymmetric azole carbocyanine dye will normally have one benzazole end group with two heteroatoms, at least one of which will be nitrogen, the other will be nitrogen, oxygen, sulfur, or selenium, where the heteroatoms will be in the one, three-positions of the azole ring. The second end group of the azole dye will normally have an aromatic ring containing at least one heteroatom, usually nitrogen, sulfur or oxygen. The asymmetric azole-indolenine carbocyanine dye will have an indolenine end group normally containing one heteroatom, including nitrogen, sulfur, oxygen or selenium, usually nitrogen. The indolenine carbocyanine will also have an azole end group, having a second heteroatom, which may be oxygen, sulfur, nitrogen or selenium.

The azole-indolenine dye will be linked to the azole dye through a hydrocarbyleneaminohydrocarbylene group of from 4 to 30, usually of from 4 to 16 carbon atoms, of from 2 to 6 hydrocarbylene groups, where the groups may be aliphatic, alicyclic or aromatic, particularly alkyleneaminealkylene linkages of from 2 to 6, usually 2 to 5, alkylene groups, particularly where at least one of the amino groups is tetrasubstituted, usually with two alkyl groups of from one to three carbon atoms, usually one to two carbon atoms, there usually being from one to five, more usually one to three alkyleneamino groups, followed by an alkylene group, where the alkylene groups will be of from two to eight, usually two to six, more usually 2 to 5 carbon atoms. A group of dyes are preferred where the terminal alkylene group of the linking group which is bound to the dye is in the range of from 2 to 6, usually 2 to 5 carbon atoms and selected for enhanced DNA affinity in gel electrophoresis and/or enhanced quenching of the donor fluorescence.

The subject compositions would generally have from about 40 to 80 carbon atoms, more usually from about 45 to 60 carbon atoms, and from 7 to 12 heteroatoms, primarily nitrogen and sulfur, although oxygen, selenium and other heteroatoms may also be present. The linking group will generally be of at least five atoms other than hydrogen, and not more than about 30 atoms other than hydrogen, usually having from about five to 15 atoms in the chain and from one to five nitrogen atoms, where one or more of the nitrogen atoms may be quaternary, preferably all of the nitrogen atoms being quaternary.

Compounds of this invention will have the following formula:

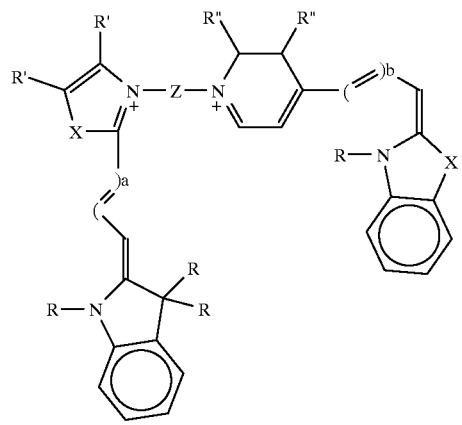

wherein:
a is from 0 to 6, usually 1 to 5, wherein the carbon atoms of the double bonds may be substituted or unsubstituted, there usually being not more than one substituent per double bond, where the substituents may have from 0 to 6, usually 0 to 3 carbon atoms and 0 to 4, usually 0 to 3 heteroatoms, which will usually include oxygen, sulfur, nitrogen and halogen, as illustrated by alkyl of from 1 to 6 carbon atoms, cyano, oxy of from 0 to 6 carbon atoms, carbonyl, both oxo and non-oxo of from 1 to 6 carbon atoms, amino and substituted amino of from 0 to 6 carbon atoms, nitro, thio of from 0 to 6 carbon atoms, imino, combinations thereof, and the substituents may be taken together to from an aromatic or alicyclic ring of from 5 to 7 annular members, e.g. butadienylene and butylene;

b is from 0 to 4, usually 0 to 3, wherein the carbon atoms of the double bonds may be substituted or unsubstituted, there usually being not more than one substituent per double bond, where the substituents may have from 0 to 6, usually 0 to 3 carbon atoms and 0 to 4, usually 0 to 3 heteroatoms, which will usually include oxygen, sulfur, nitrogen and halogen, as illustrated by alkyl of from 1 to 6 carbon atoms, cyano, oxy of from 0 to 6 carbon atoms, carbonyl, both oxo and non-oxo of from 1 to 6 carbon atoms, amino and substituted amino of from 0 to 6 carbon atoms, nitro, thio of from 0 to 6 carbon atoms, imino, combinations thereof, and the substituents may be taken together to from an aromatic or alicyclic ring of from 5 to 7 annular members, e.g. butadienylene and butylene;

each of the R groups are the same or different, R is alkyl of from 1 to 3 carbon atoms or substituted alkyl of from 1 to 12 carbon atoms and 1 to 2 heteroatoms, which are oxygen, nitrogen, sulfur, phosphorus, boron, lathanide, or other organometallic substituent;

each of the R' groups are the same or different, wherein when other than hydrogen, R' is aliphatic, alicyclic, heterocyclic or aromatic of from 1 to 12 carbon atoms and from 0 to 2 heteroatoms including nitrogen, oxygen, sulfur or selenium, and may be taken together to define an aromatic ring fused to the ring to which the R' groups are attached, the ring being of from 5 to 6 members, usually 6 members, particularly carbocyclic;

each of the R" groups are the same or different, and come within the definition of R', except that two R" groups may be taken together to define a double bond;

X may be a heteroatom or carbon atom, wherein the heteroatom may be nitrogen, oxygen, sulfur or selenium and the carbon atom is dialkyl substituted, where the alkyl group may be of from 1 to 12, usually 1 to 3, carbon atoms and from 0 to 3 heteroatoms, including nitrogen, oxygen, sulfur or selenium; and Z is a linking group comprising hydrocarbyleneaminohydrocarbylene, having from 1 to 5 amino groups, where one of more of the nitrogen atoms may be replaced with boron, lanthanide, or other metal cation, wherein the hydrocarbylene groups may be aliphatic, alicyclic or aromatic of from 2 to 12, usually 2 to 8 carbon atoms, and the nitrogen atoms are secondary, tertiary or quaternary, with N-alkyl substituents of from 1 to 6 carbon atoms;

wherein the aromatic rings may have a total of from 0 to 4 substituents of from 1 to 6 carbon atoms and 0 to 4 heteroatoms each, wherein the heteroatoms are oxygen, nitrogen and sulfur, providing for such groups as oxy, carbonyl, oxo and non-oxo, amino, nitro, thio, cyano, imino, and combinations thereof.

A preferred group of compounds have Z defined as alkyleneaminoalkylene, having from 2 to 3 amino groups, usually 2 amino groups, preferably quaternary amino, where the alkylene chains between nitrogen are of from 2 to 3 carbon atoms, particularly 2 carbon atoms, and one of the remaining alkylene chains is in the range of 2 to 6, usually 2 to 5 carbon atoms, particularly the alkylene chain bonded to the energy acceptor dye, and the number of carbon atoms is selected to provide for at least one of enhanced DNA binding affinity in gel electrophoresis and degree of quenching of the donor.

For the most part, these compounds are characterized by having when bound to DNA, absorption at a wave length greater than about 450 nm, usually greater than about 500 nm, fluorescence emission at a wavelength greater than about 600 nm, usually greater than about 625 nm, donor quenching of at least about 85%, usually at least about 90%, and a $t_{0.5}$(min) in agarose gel electrophoresis (Benson et al., (1993) *Nucleic Acids Res.*, 21, 5727–5735) of at least about 100, usually at least about 200, preferably at least about 250, more preferably at least about 300 min. For the most part, the subject compounds will have an alkylene group in the range of 3 to 6, more usually 4 to 5.

Various counterions may be employed as the anions for the positive charges of the dye. Conveniently, iodide finds use, although other halogens or other anions may find application in particular situations.

Substituents may include methyl, ethyl, propyl, hydroxyethyl, methoxypropyl, ethylthioethyl, cyanoethyl, phenyl, anisyl, ethoxycarbonylethyl, nitrophenyl, 4-aminobutyl, cyclopentyl, 2-furyl, 5-methylthiophenyl-2, ferrocenyl, lanthanyl chelate, phosphate, phosphoramidate, dimethoxyboryl, and butylselenyl.

Compounds coming within the scope of this invention include heterodimers composed of oxazole yellow, thiazole orange, thiazole blue, indolenine-azole, and indolenine-quinoline cyanines linked to indolenine-thiazole, indolenine-oxazole, and indolenine-selenazole carbocyanines.

Compounds of interest include 1-[1'-[4'-[3"-methyl-2",3"-dihydro-(benzo-1",3"-thiazole)-2"-ylidene]-methyl-pyridinium iodide]]-11-[3'-[2'[5'-1'"-methyl-3'",3'"-diethylindolenine-2'"-ylidene)-1",3"-[pentadien-1"-yl]-benzo-1'3'-thiazolium iodide]]-4,4,7,7-tetramethyl-4,7-diazaundecamethylene diiodide; 1-[1'-[4'-[3"-methyl-2",3"-dihydro-(benzo-1",3"-thiazole)-2"-ylidene]-methyl-quinolinium iodide]]-11-[3'-[2'[5'-1'"-methyl-3'",3'"-dimethylindolenine-2'"-ylidene)-1",3"-[pentadien-1"-yl]-benzo-1'3'-oxazolium iodide]]-4,4,7,7-tetramethyl-4,7-diazaundecamethylene diiodide; 1-[1'-[4'-[3"-butyl-2",3"-dihydro-(benzo-1",3"-diazole)-2"-ylidene]-methyl-quinolinium iodide]]-11-[3'-[2'[5'-1'"-methyl-3'",3'"-diethylindolenine-2'"-ylidene)-1",3"-[pentadien-1"-yl]-benzo-1'3'-thiazolium iodide]]-4,4,7,7-tetramethyl-4,7-diazaundecamethylene diiodide; 1-[1'-[4'-[3"-methyl-2",3"-dihydro-(benzo-1",3"-thiazole)-2"-ylidene]-methyl-quinolinium iodide]]-11-[3'-[2'[5'-1'"-methyl-3'",3'"-dimethylindolenine-2'"-ylidene)-1",3"-[pentadien-1"-yl]-benzo-1'3'-thiazolium iodide]]-4,4,7,7-tetramethyl-4,7-diazaundecamethylene diiodide; 1-[1'-[4'-[3"-methyl-2",3"-dihydro-(5"-chlorobenzo-1",3"-thiazole)-2"-ylidene]-methyl-quinolinium iodide]]-11-[3'-[2'[5'-1'"-ethoxyethyl-3'",3'"-dipropylindolenine-2'"-ylidene)-1",3"-[pentadien-1"-yl]-benzo-1'3'-thiazolium iodide]]-4,4,7,7-tetraethyl-4,7-diazaundecamethylene diiodide; and 1-[1'-[4'-[3"-methyl-2",3"-dihydro-(benzo-1",3"-thiazole)-2"-ylidene]-methyl-pyridinium iodide]]-11-[3'-[2'[5'-1'"-methyl-3'",3'"-dimethylindolenine-2'"-ylidene)-1", 3",5"-[heptatrien-1"-yl]-benzo-1'3'-thiazolium iodide]]-4,4,7,7-tetramethyl-4,7-diazaundecamethylene diiodide;

The subject compounds will have an affinity for dsDNA of at least about $5 \times 10^6 M^{-1}$, more usually at least about $10^7$ and greater than about $10^9 M^{-1}$ at ionic strengths of at least about 0.01, usually at least about 0.04, preferably at least about 0.2 at 25° C. Gel electrophoresis is usually performed at an ionic strength of about 0.04.

These compounds find use as labeling agents, where the compounds are used in a process for detection of nucleic acid or as a label which is prepared for labeling a compound to provide a fluorescent signal.

The first situation is exemplified by separations employing an electrical field, e.g. electrophoresis. In employing the subject compounds, the nucleic acid, usually dsDNA, and the dye may be brought together in an appropriately buffered medium and incubated for sufficient time for the dye to non-covalently bind and intercalate in the nucleic acid for prestaining. The ratio of dye to ds nucleic acid may be varied widely ranging from about one molecule of dye per four base pairs, to as little as one molecule of dye per 200 base pairs, usually ranging from about one dye molecule per 4 to 100 base pairs, depending upon the desired degree of sensitivity, size and nature of the nucleic acid molecule, choice of dye, manner of measuring, period of time for the electrophoresis, and the like. Dye present in excess of one dye per four base pairs, or more, does not significantly influence the observed signal, so that any increase in the amount of dye above a mole ratio of one dye molecule per four base pairs will normally be undesirable. Generally, the amount of dye will range from about one molecule per 4 to 50 base pairs for optimum results. It is important that large excesses of dye to nucleic acid base pairs and high concentrations of nucleic acid be avoided, as this can lead to precipitation of the nucleic acid, particularly when applying the sample to the gel.

The subject dyes may be used in electrophoresis, with dsDNA having as few as about 70 bp, with no upper limit.

The time for the gel electrophoresis with prestained dsDNA will vary inversely proportional to the smaller size of dsDNA to be detected, where the time will generally be in the range of about 2 to 60 min, the longer times being associated with the larger DNA being the minimum DNA to be detected.

The amount of nucleic acid will generally be conventional amounts employed for electrophoresis, generally ranging from about 0.005 ng/$\mu$l to 5 ng/$\mu$l. Various conventional buffers may be employed, such as Tris-acetate or Tris-borate, generally present in the range of about 1 to 50 mM, more usually in the range of about 1–40 mM, to provide a pH in the range of about 5 to 10, more usually about 7 to 9. Also, a metal ion chelator may be present in minor amount, generally from about 0.05 to 0.5 mM. Conveniently, EDTA may be employed.

The dye and nucleic acid may be incubated, usually for at least 5 minutes and not more than about 2 hours, where complex formation will normally be complete in less than about one hour, usually in about 30 min., at room temperature. The incubated solution may be used directly or further diluted, as appropriate, prior to application to the gel.

Tracking dyes are preferably not used, since it is found that the tracking dyes may tend to interfere with the detection of the non-covalently bound and intercalated dye. Also, gels may be subjected to pre-electrophoresis for sufficient time to decrease background fluorescence, usually not more than about three hours.

The electrophoresis may be performed in any convenient and conventional manner, where the bands may now be detected by fluorescence of the non-covalently bound and intercalated dye. The electrophoresis insures that unbound dye is removed from the region of the bands and the dye is found to be retained by the nucleic acid, so that individual bands may readily be detected by fluorescence scanning. The irradiation and detection system will be directed to excitation in the range of about 450–500 nm and detection in the range of about 650–700 nm. Thus, a convenient laser can be employed, such as an argon laser which provides for coherent light at 488 nm. When using thiazole orange as the absorbing moiety, the excitation light wavelength will be at or about 485–490 nm.

Of particular interest is the use of a confocal laser scanning fluorescence imaging system. A system which has been found to be convenient employs a long pass dichroic beam splitter to reflect the laser beam down through a microscope objective and onto the sample. The fluorescence emission is collected by the objective and passed through the beam splitter to a photodetector. The fluorescence emission is then passed through a spatial filter to effect confocal detection and a long pass or bandpass color or interference filter before reaching a photomultiplier tube. An appropriate servo motor-driven XY translation stage is employed with a 2.5 $\mu$m resolution to translate the gel past the laser beam at a convenient speed, generally about 1–5 cm/sec. A microcomputer may be employed to control the XY translation stage and to acquire and display images. The fluorescence images may then be pseudo-color encoded to represent different intensity levels and contrast stretched with a histogram equalization method to enhance the images. To quantitate the image data, the image columns that enclose the nucleic acid bands may be extracted and integrated.

The nucleic acid may be readily isolated free of the intercalated fluorescent dye for further use. One may use the Geneclean® kit for recovery of 50% or better of the nucleic acid. By combining the intercalated dye containing nucleic acid with Glassmilk in an aqueous solution of alkali metal iodide, e.g. 1–10 ng nucleic acid (1–5 $\mu$g/ml nucleic acid) and about 1–10 $\mu$g/ml of Glassmilk, incubating with agitation for about 5–60 mins. followed by centrifugation, resuspending the resulting pellet in an appropriate ethanolic buffered aqueous solution (e.g. 1:1) followed by centrifugation and repeating this washing procedure, the nucleic acid is obtained substantially free of the fluorescent dye.

By virtue of the use of the subject binding fluorescent dyes in the electrophoresis, greatly enhanced sensitivities are achieved due to the much higher level of fluorescence intensity which is obtained. Sizes and amounts of DNA fragments in mixtures of unknown composition can be determined with a total amount of material ranging from 100 pg to 1 ng depending on the complexity of the mixture and the size range of the fragments. Thus, the subject method can find application in the detection of nucleic acid of less than about 5 ng, particularly less than about 1 ng, frequently less than about 100 pg, even less than about 50 pg.

Instead of employing the subject dyes for detection of nucleic acid bands in electrophoresis, compositions comprising dsDNA and the subject dyes at substantial saturation may be employed, where the dsDNA is joined to an entity for binding to another entity, either covalently or non-covalently. The entities will be either referred to as specific binding pairs, since the entities will have specific affinity for a complementary entity, as compared to diverse other types of molecules, or covalently binding functionalities for reacting with other molecules, such as polypeptides or saccharides.

The specific binding pairs may involve a wide variety of molecules, which are arbitrarily called ligands and receptors. For the subject invention, the ligands and receptors may include a wide variety of proteins, such as antibodies, specific binding proteins, such as surface membrane protein receptors, lectins, blood proteins, and the like, carbohydrates, small organic molecules, both naturally occurring and synthetic to which proteins specifically bind, either naturally occurring protein receptors or antibodies, nucleic acids which may hybridize or specifically bind to an homologous or partially homologous sequence usually having at least about 30% complementarity, preferably at least about 50% complementarity over the complementary region, and the like. In effect, any two molecules which have a specific binding affinity may be employed, so that the label may be used for detection of the presence of the complementary member. The desired specificity may be varied widely, depending upon the particular nature of the molecules to be detected, the information desired about the nature of the sample, or the like.

The labels may be used for detecting any of a wide variety of molecules in a wide variety of samples, which includes physiological samples, e.g. blood, plasma, urine, spinal fluid, saliva, feces, mucus, etc., waste samples, from processing, garbage, soil, water, etc., contaminants in products, such as food, drugs, etc.

Depending upon the fluorescence intensity one desires, one can vary the length of the dsDNA and the level of non-covalent binding and intercalation to increase the fluorescence intensity per molecule. Usually, there will be at least about 16 base pairs, more usually at least 20 base pairs, and one may have dsDNA of at least about 1 kbp or even 2 kbp or more. The particular length of the dsDNA is not critical to this invention and may be varied in accordance with the fluorescence intensity desired per molecule, purpose of the label, convenience, and the like. With some dyes there can be an increase in fluorescence intensity by having A-T pairs. Thus, one may provide for a poly A-T.poly A-T dimer to be used as the label. However, if one wishes to further increase the stability of the dsDNA, beyond that which the intercalating dimer provides, one can use a combination of AT and GC pairs or a poly G-C.poly G-C dsDNA. Alternatively, one may use any source of random DNA, such as calf thymus DNA, *E. coli* DNA, etc.

The dsDNA should provide for means for binding to another molecule. This can be achieved in a wide variety of ways, depending upon the manner in which the label is to be employed. For example, the dsDNA may include biotin conjugated nucleotides, one or more biotins, where the biotin will bind to avidin or streptavidin (hereafter both will be referred to as "avidin"). The biotins may vary from one biotin per nucleotide to 0.1% of the nucleotides depending on the nature of the procedures, conditions, etc. Alternatively, any molecule may be employed, particularly a small organic molecule (less than about 2 kdal) which is unlikely to be encountered in the sample of interest, where the small organic molecule has a specific receptor or antibody, particularly monoclonal antibody, to which it specifically binds. Thus, thyroxine, corticosteroids, estrogens, retinoic acid, mannose and the like may be used with proteins which bind specifically to such molecules. Alternatively, synthetic or naturally occurring molecules may be employed for which antibodies have been produced, such as 2,4-dinitrophenyl, barbiturate, phosphatidylcholine, digoxigenin, etc. These molecules may be included during synthesis of the DNA by being linked to an internal or terminal nucleotide, where the DNA is synthesized in accordance with conventional automatic procedures, or may be added after synthesis of the DNA by linking either available hydroxyl or amino groups.

The binding entity may be an active functionality for covalently bonding to a molecule having a functionality capable of forming a stable covalent link, such as amino, hydroxyl, thio, carboxyl, activated olefin or aryl, or the like where the functionality to other than a naturally occurring functionality of the nucleotide. The label may be modified with an activated olefin, such as maleyl, for reaction with a thiol group, a carboxyl for reaction with an amine, or the like. In this manner, many different types of molecules may be fluorescently labeled for use in diagnostics, both competitive assays and non-competitive assays, histology, cytology, separations e.g. electrophoresis, HPLC, FACS, and the like.

The strands of DNA may take various structures. In many situations, the dsDNA may comprise two strands, where the strands may be completely or only partially overlapping, where the ends may extend in the 5' and/or 3' directions, so that one strand may be substantially longer than the other strand, where the other strand may bind either 5' proximal, 3' proximal or centrally. Alternatively, the two strands may overlap to provide for staggered ends, where the single stranded portions of the DNA may then be used to bind to complementary sequences. Alternatively, one may provide a single strand with an inverted repeat, so that the strand loops back on itself to provide the double stranded portion. The hairpin structure may be used solely for labeling, or a single stranded portion of the hairpin may be employed for hybridizing to a complementary sequence. The hybridizing single stranded portion may be an extension at either the 5' or 3' end to provide for a staggered terminus or may be present in the loop of the hairpin.

The subject labels may be used in a wide variety of environments and contexts to provide for high levels of fluorescence intensity without interference from the molecules to which the labels bind, either directly or indirectly, the media employed, the conditions employed, and the like. Thus, the subject labels may be employed in specific binding pair assays, where the label may be readily linked to another molecule through a specific binding pair combination. For example, in diagnostic assays, one may combine an avidin conjugated antibody, where the antibody binds to a molecule of interest, to biotin labeled DNA dye aggregate to provide for fluorescent labeled antibody.

Alternatively, the antibody may be labeled with biotin, so that avidin may act as a bridge between the biotin labeled antibody and the biotin labeled DNA dye aggregate. In this way, the fluorescent label may be added after combining the sample with a complementary specific binding pair member and carrying out the assay, followed by addition of label and removal of any nonspecifically bound label.

Where a single stranded DNA sequence is provided as part of the label, this can be used for hybridizing to complementary DNA or RNA sequences. The presence of the non-covalently bound and intercalated dye greatly enhances the stability of the dsDNA. Thus, one can introduce the subject labels into a denaturation medium under conditions where the non-covalently bound and intercalated dsDNA will be stable, while the sample DNA may be denatured to provide for single strands. Where single stranded DNA or RNA is present, there will be no need for providing for denaturation conditions. Therefore, the subject molecules may be used as probes to identify DNA sequences under a wide variety of conditions, including electrophoresis, polymerase chain reactions, where the single stranded sequence may serve as a primer, in Southern blotting, Northern blotting and the like.

Instead of having non-covalent complexes between the non-nucleic acid specific binding pair member and the DNA dye aggregate, one can provide for covalent bonding. Thus, by providing for activated groups such as carboxy, diazo, activated ethylene, or the like, the fluorescent moiety may be readily linked to other molecules, such as proteins, sugars, lipids, or the like by employing conventional linking groups resulting in amide, amines, diazo, esters, thioethers, and the like. For example, one may introduce a thiol group at either the 3' or 5' terminus of a synthetic oligonucleotide, synthesize the complementary strand and form a non-covalently bound and intercalated dye complex. The thiol group on the DNA can then be reacted with a maleimide modified protein, e.g. an antibody. Other techniques may follow conventional procedures found in the literature.

One may also use the subject labels in a fluorescence activated cell sorter to provide for greatly enhanced sensitivity as a result of the substantially increased fluorescence intensity. Again, one may use ligands for surface membrane receptor proteins, sugars for lectins, antibodies for epitopes present on the surface of the cell, or the like, where the subject labels may be bound covalently or non-covalently to the molecule which binds to the cell component.

With the subject compositions one can also detect proteins to transcriptional initiation elements, e.g. promoters, operators, enhancers, etc. By having labeled dsDNA, according to the subject invention, mixed with labeled proteins, labeled with a fluorescent molecule emitting at a different wavelength from the non-covalently bound and intercalated fluorescer, or other appropriate label, one can determine the presence of transcription factors and cofactors. For example, one can gel electrophorese the mixture and identify the presence of the protein bound to DNA by virtue of the double labeling.

One may also use the subject fluorescent non-covalently bound and intercalated DNA for in situ hybridization studies, intermolecular transfer of fluorescent molecules from one doubly stranded nucleic acid molecule to another, e.g. for transferring fluorescent dye without the fluorescer being transferred to the medium. This may find use in making chromosomes with triplex formation, in transferring to nucleic acid in a gel or on a membrane, etc. The fluorescer intercalated DNA may be bound to a particle, e.g. magnetic, to be removed after use as transfer agent.

The subject labels may be used with advantage with a confocal fluorescence imaging system, as described previously. With the subject compounds, substantially less than 100 pg of DNA can be detected, usually less than about 50 pg, but more than about 10 pg.

In histology and cytology the subject fluorescent labels provide for high sensitivity in detecting target epitopes, particularly at low levels.

The subject compositions may be synthesized in accordance with conventional techniques. See, for example, Glauert and Mannn (1952) *J. Chem. Soc.* 5012; Brooker et al. (1942) *J. Am. Chem. Soc.* 64, 199–210; Brooker et al. (1941) *ibid* 63, 3192–3203; Rye et al. (1992) *Nucleic Acids Res.* 20, 2803–2812. Particularly, the activated methyl groups of N-substituted methylindolinium and methylbenzothiazole, may be linked through carbylene groups to various end groups to form the asymmetric cyanine dyes by displacement of anil groups. The carbocyanine azole-indolenine dye can be linked to a cyanine, xanthine, rhodamine, phenoxazine or other dye through a hydrocarbyleneaminohydrocarbylene group by a variety of approaches, conveniently by substituting one of the dye moieties with a hydrocarbyleneamino or polyhydrocarbyleneamino group and linking the other dye moiety through a haloalkyl group.

The subject compounds can be provided in kits, where a multiplicity of the subject compounds, by themselves or in combination with other compounds may be provided. In many of the applications discussed above there is an interest in being able to detect a plurality of targets in a single sample. Therefore, it is desirable to use a single irradiation source, while at the same time being able to obtain fluorescence at different distinguishable wavelengths. In this way, at one time one can detect the presence of one or more moieties of interest.

The dyes of the subject invention and/or analogous heterodimeric dyes may be employed, where one or both of the chromophores are based on combinations of: (1) indolenine-benzoheteroazole linked by different numbers of methines; (2) quinolinium-benzoheteroazole linked by different numbers of methines; and (3) benzoheteroazole-benzoheteroazole linked by different numbers of methines. The "hetero" will be oxygen, nitrogen or sulfur, usually sulfur, and the number of methines will be in the range of 1 to 7, usually 1 to 5. In the heterodimeric dyes, the linking group between the two chromophores is as described previously for the subject indolenine dyes, except that the hydrocarbylene of the hydrocarbyleneaminohydrocarbylene is alkylene, and the alkylene groups need not be all the same, in fact, the alkylene group bonded to a chromophore is selected by empirical determination to optimize the donor dye quenching and/or affinity to DNA, particularly in relation to gel electrophoresis. Usually, at least one alkylene group will be different from the other alkylene groups. The linking group will usually have at least about 12 atoms, more usually at least about 13 atoms in the chain and not more than about 18 atoms, more usually not more than about 16 atoms in the chain.

As exemplified in the subject invention, a number of dyes are provided which use thiazole orange as the donor, since thiazole orange has a strong absorption maximum when bound to DNA at about the wavelength of the 488 nm argon ion laser line. By varying the acceptor dye and the length of the linking chain a group of dyes is provided which have a strong absorption maximum at a common wavelength, a strong affinity (low off rate) to DNA during gel electrophoresis, fluoresce at different wavelengths with high efficiency in the red-to-infrared region and have strong quenching of the donor dye. The donor chromophores are conveniently benzoheteroazole-quinolinium dyes, although the other chromophores indicated above may also serve as donor dyes. Any of the chromophores indicated above may serve as acceptor chromophores, where the donor and acceptor chromophores are different. Of particular interest are dyes which emit at a wavelength greater than about 600 nm, preferably greater than about 625 nm, more preferably greater than about 650 nm, and usually below about 800 nm. In this way detection can be achieved with dyes emitting for detection in the green and red channels without significant cross-talk between the channels.

The benzoheteroazole-quinolinium unsymmetrical cyanine dyes as one member of a dimer have been the subject matter of a prior patent (U.S. Pat. No. 5,401,847), where the alkylene group in question is 3 carbon atoms and all the alkylene groups are the same. As shown in the experimental section, where the alkylene group is 5 carbon atoms, a large increase in binding affinity and enhanced donor quenching are observed.

The kits will have at least two dyes, usually 3 or more dyes, generally not more than 6 dyes, of which at least 2 dyes absorb at about the same wavelength and emit at wavelengths which differ by at least 10 nm, usually at least about 15 nm. The dyes will be selected when used in gel electrophoresis to have a higher or the highest $t_{0.5}$ of the series in the number of carbon atoms in the alkylene group bonded to one of the chromophores, particularly the acceptor chromophore. The particular donor may be varied widely depending on the desired wave length absorption maximum, the effect on binding affinity to DNA, the efficiency of quenching by the acceptor or energy transfer to the acceptor, ease of synthesis, the nature of the combinations of dyes in the kit, and the like. The kits will include at least one heterodimeric dye, and may also include one or more homodimeric dyes.

Instead of providing the combinations of dyes as substantially pure compounds, the dyes may be provided complexed to dsDNA or analog thereof, generally at a ratio of 1 dye:4–200 bp, more usually 1 dye:5–100 bp, where the dsDNA will usually be at least about 6, usually at least about 8 bp, and may be 1000 kbp or more, usually being in the range of about 8 bp to 50 kbp. The dsDNA may be covalently bonded to one or more members of a specific binding pair, such as biotin and strept/avidin, ligand and antibody, substrate and enzyme, ligand and receptor, etc. In this way the dye complexed DNA may be used as a label in the various applications previously described.

As individual novel compounds are those members of the alkylene series which have improved properties as compared to their known analogs, as exemplified above. Thus, for fluorescent heterodimers having an unsymmetrical cyanine dye as one member, the subject compounds are characterized by having an alkylene group bonded to one or both of the chromophores of the heterodimeric dye which provides for the improved properties discussed above. For the most part, the novel compounds will have alkylene groups within the linking group which are different, generally having 1 to 3, usually 2 alkylene groups which are of from 2 to 3 carbon atoms, and 1 to 2, usually 1 alkylene group, particularly bonded to a chromophore, of from 3 to 6 carbon atoms, usually 3 to 5 carbon atoms, and more usually 4 to 5 carbon atoms.

The dyes are shown to have a number of advantages in gel electrophoresis. The dyes do not exhibit significant sequence specificity. For a given series of homologous dyes, the mobility shift is unaffected by the stepwise change in the length of the linker. In addition, the mobility shift is similar for dyes with similar linkers but very different chromophores. The maximum discrepancy between the actual and estimated fragment sizes in multiplex sizing of dsDNA fragments observed with the subject dyes of the kits is about 5%. A systematic adjustment of 5% to the mobility values in a multiplex dsDNA sizing using TOTO and TOTIN allows for sizing with an error of less than 1.3%.

The following examples are offered by way of illustration and not by way of limitation.

EXPERIMENTAL

EXAMPLE 1

Synthesis and Properties of TOTIN-5 (also designated 17a)

Materials and Methods 2,3,3-Trimethyl indolenine, methylbenzothiazole, iodomethane, and diidopropane were purchased from Aldrich and used without further purification.

Malonaldehyde dianil was synthesized according to literature reports (Glauert, R. H. and Mann, F. G. J. Chem. Soc. (1952) 5012, by the method of Claisen (Ber. (1903) 36, 3664). Dry nitrobenzene was freshly distilled from $CaH_2$. Dry triethylamine was distilled from $Na°$. DMF was pre-dried with $MgSO_4$, fractionally distilled and stored over molecular sieves. All dry solvents were stored under $N_2$. All reactions were run under anhydrous conditions under $N_2$. Reactions were monitored by TLC (silica gel 60, $A_{260}$, Fisher) and visualized with short and long wavelength UV irradiation. Flash column chromatography was performed on silica gel 60 (200–440 mesh Fluka).

Synthesis

Scheme 1 (FIG. 1) outlines the synthesis of iodopropyl-TIN-5. 2,3,3,-Trimethylindolenine (1) reacted with 3 equivalents of iodomethane in refluxing anhydrous ethanol to produce 2 in 90% yield. Compound 2 reacted with 1.1 equivalent of malonaldehyde dianil in refluxing $Ac_2O$ to produce a quantitative yield of compound 3. Methyl benzothiazole (4) was alkylated with 3 equivalents of diiodopropane in dry nitrobenzene overnight at 140° C. to give 5 in 87% yield. Compounds 3 and 5 reacted with mild heating in the presence of 2 equivalents of triethylamine to produce iodopropyl-TIN-5 2-[5'-(3"-iodopropyl(benzo-1",3"-thiazole)-2"-ylidene)-1',3'-pentadien-1'-yl]-methyl-3,3-dimethylindoleninium iodide. Iodopropyl-TIN-5 was purified by flash chromatography eluting with methanol/$CH_2Cl_2$ (1:20 v/v). The pure iodopropyl-TIN-5 was recrystallized from methanol:$CH_2Cl_2$(1:10 v/v)/ether to give TIN-5 in a 73% yield as a deep blue powder.

Figure 2:
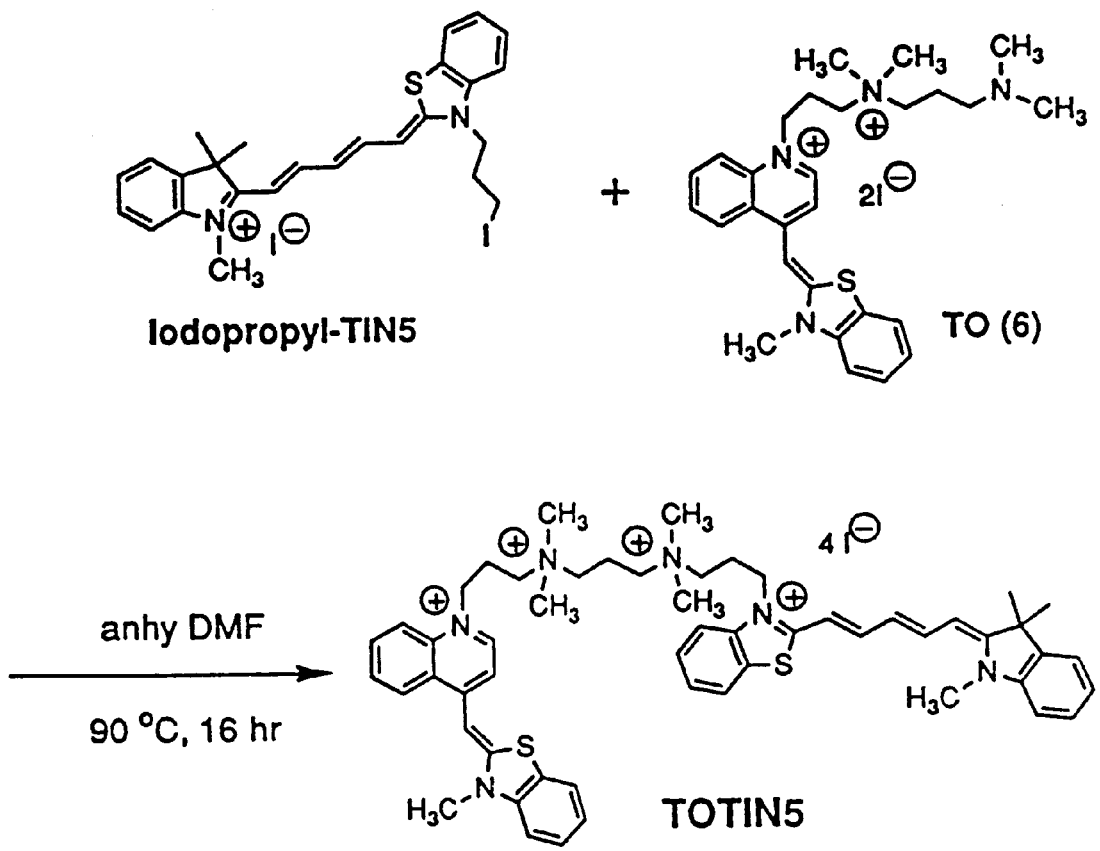
FIG. 2 (Scheme 2) is a scheme for the synthesis of TOTIN-5 heterodimer (also designated as TOTIN 17a) by the reaction of (tetramethylpropanediamino) propyl thiazole orange (TO6) with (TIN-5)

Scheme 2 (FIG. 2) outlines the synthesis of the TOTIN-5 (17a) heterodimer by the reaction of (tetramethylpropanediamino)propyl thiazole orange, TO(6), described previously (Benson, S. C., Singh, P., and Glazer, A. N. (1993) *Nucleic Acids Res.* 21, 5727–5735), and 1.2 equivalents of iodopropyl-TIN-5 in anhydrous dimethylformamide. After 16–24 hours at 90° C., the crude product was precipitated from the reaction mixture with ether/petroleum ether and purified by flash chromatography employing EtOAc: AcOH: $H_2O$: $NEt_3$ (1:2:2:0.2). The pure product was recrystallized from methanol:$CH_2Cl_2$(1:10 v/v)/ether to give a 73% yield of TOTIN-5 (17a), 1-[1'-[4'-[3"-methyl-2",3"-dihydro-(benzo-1 ",3"-thiazole)-2"-ylidene]-methyl-quinolinium iodide]]-11-[3'-[2'[5'-1'''-methyl-3''',3'''-dimethylindolenine-2'''-ylidene)-1", 3"-[pentadien-1"-yl]-benzo-1'3'-thiazolium iodide]]-4,4,7,7-tetramethyl-4,7-diazaundecamethylene diiodide. No monomeric starting material was detected in the purified TOTIN-5 (17a) by thin layer chromatography with EtOAc: AcOH: $H_2O$ (1:2:2 v/v) or methanol: $CH_2Cl_2$/(1:10 v/v). The electrospray mass spectrum (skimmer voltage=40 V) of TOTIN-5 (17a) had major fragment peaks resulting from cleavage of the tetramethyldiaminopropyl linker to produce intact donor and acceptor fragments containing singly charged cations with dimethylaminopropyl side chains. The mass spectrum of TOTIN-5 (17a) contained dimethylaminopropyl-TO ($C_{26}H_{34}N_3S+=376$) and dimethylaminopropyl-TIN ($C_{26}H_{34}N_3S+=444$).

Absorption spectra of Iodopropyl-TIN-5 and TOTIN-5

To obtain the absorption spectra of iodopropyl-TIN-5, pure recrystallized iodopropyl-TIN-5 (4.8 mg, mw=654) was dissolved in 50 ml MeOH to give a stock solution ($1.47 \times 10^{-4}$ M). A molar extinction coefficient of 230,200 at $\lambda_{max}=643$ nm was determined on diluted sample (⅟₅₀) in MeOH. The solvent dependence of the absorption spectrum of TIN-5 was determined by running equal aliquots of the stock solution in MeOH, 4 mM Tris-acetate-0. 1 mM ethylenediamine tetraacetate buffer, pH 8.2 (TAE), or buffer plus calf thymus dsDNA at 20 base pairs (bp):dye. The following table indicates the results.

TABLE 1

Absorption data for TIN-5 and TOTIN.[1]

| Dye | Solvent | $\lambda_{max}$ nm | $\epsilon$ $M^{-1}cm^{-1}$ |
| --- | --- | --- | --- |
| TOTIN-5 | MeOH | 288 | 17,900 |
|  |  | 506 | 79,000 |
|  |  | 647 | 146,400 |
|  | TAE | 289 | 15,300 |
|  |  | 508 | 69,600 |
|  |  | 649 | 126,500 |
|  | TAE/DNA | 515 | 60,000 |
|  |  | 653 | 102,300 |
| TIN-5 (17a) | MeOH | 318 | 11,500 |
|  |  | 643 | 230,200 |
|  | TAE | 318 | 9,200 |
|  |  | 639 | 172,800 |
|  | TAE/DNA | 651 | 142,600 |

[1]All spectra in MeOH and TAE (4 mM TAE buffer pH 8.2) were at room temperature with dyes at ~3 × 10⁻⁶ M. Spectra of dyes bound to dsDNA (3 × 10⁻⁶ M dye) were with calf thymus DNA (6 × 10⁻⁵ M bp) at 20 bp:dye, in 4 mM TAE buffer pH 8.2, recorded at room temperature after incubation of the dyes with the DNA for 15 minutes in the dark.

The 450–550 nm region of the absorption spectrum of the TOTIN-5 heterodimer (17a) was closely matched by addition of the absorption spectra of the two monomers run at equal molar concentrations. Therefore, the molar extinction coefficient TOTIN-5 (17a) in MeOH ($\lambda_{max}$abs=507 nm, $\epsilon=79,000$) was calculated from the known extinction coefficients of TO (Benson et al. (1993), supra) and iodopropyl-TIN-5 at 507 nm. The solvent dependence of the absorption spectrum of TOTIN-5 (17a) was determined as for the TIN-5 monomer (Table 1).

Fluorescence Emission Spectrum of TOTIN-5 (17a) Determined under Different Conditions The calf thymus DNA:TOTIN-5 (17a) complex was formed at 1 dye: 100 bp DNA. In this complex, TOTIN-5

(17a) showed a 36 fold enhancement of 672 nm fluorescence emission (for 488 nm excitation) relative to that of the free dye (4 mM TAE, pH=8.2, $\lambda_{max}$ em (free)=665 nm). The intensity of TIN-5 emission at $\lambda_{max}$ em=672 nm per mole of dsDNA bound TOTIN-5 (17a) was found to be nearly constant for dye bound from 100 to 5 bp:dye.

At 488 nm, there is negligible direct excitation of the TIN-5 chromophore; virtually all of the energy is absorbed by the thiazole orange chromophore. At low saturation of binding sites, the observed energy transfer from TO to TIN-5 originates within a dimeric molecule. The comparison of the relative emissions at 532 nm (TO) and 672 nm (TIN-5) established that such transfer is indeed very efficient. Under these conditions, the ratio of thiazole orange donor emission at 532 nm to TIN-5 acceptor emission at 672 nm is 1:2.7. As the ratio of dye to DNA bp increased to 1:5, quenching of the TO emission at 532 nm increased to >98% and the ratio of donor to acceptor emission decreased to 1:35 (FIG. 3).

Stability of the TOTIN-5(17a)-DNA Complex during Agarose Gel Electrophoresis

The stability of dsDNA-dye complexes to electrophoresis was examined as described by Benson, S. C., Mathies, R. A., and Glazer, A. N. (1993) *Nucleic Acids Res.* 21, 5720–5726. Measurement of the off-rate of dye during electrophoresis of complexes of λDNA-HindIII restriction fragments with TOTIN-5 (17a), performed at a ratio of 1:20 dye:DNA bp, gave a $t_{0.5}$ of 114 min.

In FIG. 3A, the solid curve shows the absorption spectrum of TOTIN-5 (17a) ($6 \times 10^{-6}$ M) bound to calf thymus DNA ($3 \times 10^{-6}$ M bp) at 20 bp:dye at 4 mM TAE buffer pH 8.2. The dashed curve represents the fluorescence emission spectrum of the dye ($2 \times 10^{-7}$ M) on excitation in 488 nm in 4 mM TAE pH 8.2, when bound to calf thymus DNA ($2 \times 10^{-5}$ M bp) at 100 bp:dye. All spectra were recorded at room temperature after incubation of the dyes with the DNA for 15 min. in the dark. The intensities at the $\lambda_{max}$ of the TO donor chromophore absorption (507 nm) and emission spectra (532 nm) were arbitrarily equalized.

In FIG. 3B, λDNA/HindIII fragments (4 ng; 800 pg/μl, 5 μl aliquots) complexed to TOTIN-5 (17a) at 1 dye: 20 bp in 50 mM NaCl, were loaded at consecutive 15 min. intervals and electrophoresed over 140 min. The logarithm of the integrated fluorescence intensity of the bands is plotted against electrophoresis time of the fragments. The slope of the linear fit of the data gives a $t_{0.5}$ of 114 min. for the dsDNA-TOTIN-5 (17a) complex. For other experimental details, see Benson et al. (1993), supra.

The dependence of donor and acceptor fluorescence emission of TOTIN-5 (17a) as a function of fractional saturation of binding sites in dsDNA was determined. Fluorescence emission spectra of the dye ($2 \times 10^{-7}$ M) upon excitation at 488 nm in 4 mM TAE pH 8.2 was determined, when the dye was bound to decreasing concentrations of calf thymus DNA at various bp:dye ratios. Spectra were recorded at room temperature after incubation of the dye with the DNA for 15 min. in the dark and the fluorescence intensities were recorded at the emission maximum at 672 nm for TIN-5 and 532 nm for TO.

The above results show that the subject composition provide a new class of dicarbocyanine dyes with high dsDNA binding affinity and particularly favorable spectroscopic properties for fluorescence detection in the far red region of the visible spectrum. The acceptor TO chromophore in TOTIN-5 (17a) is a dicarbocyanine dye which contains a non-planar, sterically bulky, εem dimethyl substituted indolenine group coupled to a planar benzothiazole by a pentamethine bridge.

TOTIN-5 (17a) is found to be superior to the best DNA-binding energy transfer dye reported, TOTAB (Benson et al. (1993) supra), which was designed for strong absorbance at 488 nm, a large Stokes shift and strong fluorescence emission. TOTAB and TOTIN-5 (17a) complexes with dsDNA, at 1 dye:20 DNA bp, have similar stabilities to agarose gel electrophoresis; $t_{0.5}$ values of 124 min. and 114 min., respectively. The two heterodimers have the same molar extinction coefficient ($\epsilon_M$) at 488 nm, but the TIN-5 chromophore in TOTIN-5 (17a) has an $\epsilon_M$ two-fold higher than the thiazole blue (TAB) chromophore of TOTAB. Evidently the fluorescence quantum yields of TOTIN-5 (17a) and TAB are near-equivalent, because on 488 nm excitation of equimolar solutions of their dsDNA complexes, the emission from TOTIN-5 (17a) is also twice as high as that from TOTAB. The TOTIN-5 (17a) dye has the further advantage that TIN-5 emission in DNA-bound TOTIN-5 (17a) is not quenched even at one dye:5 DNA bp in contrast to the strong quenching of the TAB emission of TOTAB at high saturation of dsDNA binding sites. In addition, the TOTIN-5 (17a) fluorescence emission maximum (672 nm) lies 12 nm further to the red than that of TOTAB (660 nm).

EXAMPLE 2

Synthesis and Properties of TOTIN 17a–c, TOTAB 18a–d, TOSTAB 19 and TOTAG 20

Materials 1,2,3,3-Tetramethylindolenine, lepidine, quinaldine, 2-methylbenzothiazole, iodomethane, diiodopropane, diiodobutane, diiodopentane, N,N'-tetramethyldiaminopropane, propiolaldehyde diethyl acetal, aniline hydrochloride, 1-chloro-2,4-dinitrobenzene, diphenylformamidine, and ethidium bromide were purchased from Aldrich and used without further purification. Malonaldehyde dianil and gluconaldehyde dianil were synthesized according to literature reports. Glauert & Mann, F.G. (1952) *J. Chem. Soc.* 5012. Absolute EtOH was used as purchased. Dry nitrobenzene was freshly distilled from $CaH_2$. Dry triethylamine was distilled from Na°. DMF was pre-dried with $MgSO_4$, fractionally distilled and stored over activated molecular sieves. Acetic anhydride was fractionally distilled. All dry solvents were stored under dry $N_2$. All reactions were run under anhydrous conditions under dry $N_2$. Reactions were monitored by TLC (silica gel 60, $A_{254}$, Fisher) and spots on developed plates were visualized with short and long wavelength UV irradiation. Flash column chromatography was performed on silica gel 60 (200–440 mesh, Fluka).

Studies of DNA-dye interactions in solution

TAE buffer refers to 4 mM (1×) Tris-acetate-EDTA, pH 8.2 prepared by appropriate dilution of a stock TAE solution (10×) containing 2M tris(hydroxymethyl)aminomethane-0.05M $Na_2EDTA$ titrated to pH 8.2 with glacial acetic acid. Calf thymus DNA (Sigma) was dissolved in TAE buffer, and sheared by repeated passage through a small gauge needle. The DNA was extracted with phenol/$CHCl_3$, precipitated with ammonium acetate/isopropanol at 0° C., and resuspended in 40 mM TAE. Stock double-stranded DNA (dsDNA) solutions were stored at −20° C. DNA concentrations were calculated assuming that 50 ug/ml gave one absorbance unit per cm at 260 nm. The molar base-pair (bp) dsDNA concentration was based on a molecular weight of 635 gm/mole bp. Concentrated stock solutions of dyes ($10^{-4}$ M in MeOH or DMSO) were stored at −20° C. Freshly diluted stock dye solutions ($10^{-6}$ M) were prepared in 4 mM TAE, pH 8.2, immediately before use.

Absorption and fluorescence measurements on solutions

Absorption spectra were determined with a Perkin-Elmer Lambda 6 spectrophotometer. Uncorrected fluorescence measurements with a Perkin-Elmer model MPF 44B spectrofluorimeter in ratio mode interfaced with a Macintosh IIci by Lab Ware software. All spectra were taken at room temperature.

Synthesis of monomer dyes

Figure 4:
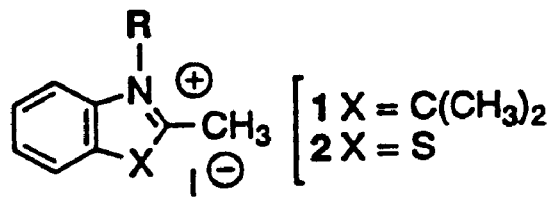
FIG. 4 is the formulae of reactants used in the synthesis of the cyanine dyes shown in FIG. 5.
Figure 4:
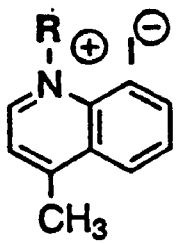
Figure 4:
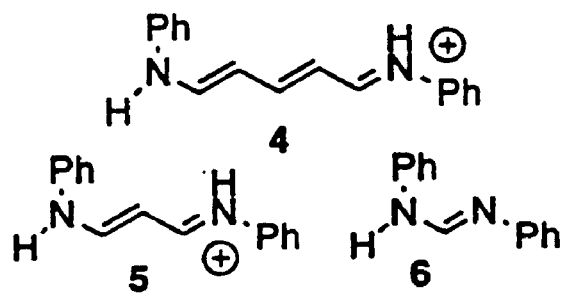
Figure 10:
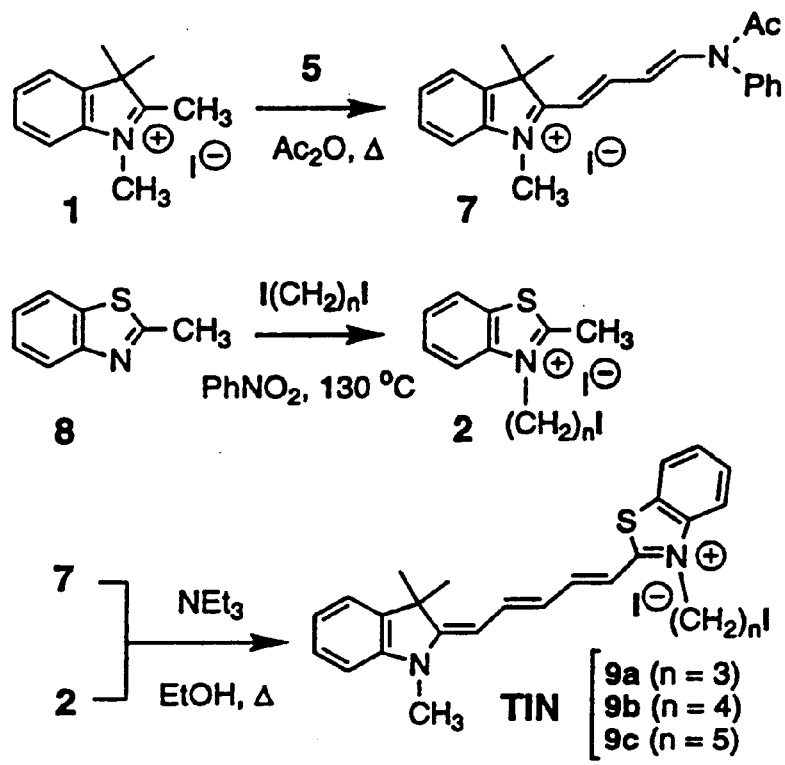
FIG. 10 (Scheme 3) is a flow chart of the synthesis of benzothiazoleindolenine derivatives according to the subject invention.

Scheme 3 (FIG. 10), which employs the intermediates in FIG. 4 for the synthesis of the TIN 9 (thiazole-indolenine) derivatives, exemplifies the general procedure used for the synthesis of cyanine dyes. The procedure followed well-established literature methods with only slight modifications. Brooker et al. (1942) *J. Am. Chem. Soc.* 64, 199–210; Brooker et al. (1941) ibid. 63, 3192–3203. Quaternized nitrogen heterocycle derivatives 1–3 react with conjugated dianil derivatives 4–6 in refluxing acetic anhydride yielding intermediate acetanilide derivatives such as 7 (Scheme 3). In a second step, the cyanine dye is formed when compounds 1–3 react with the acetanilide derivatives (7) with elimination of acetaniline. For example, as shown in Scheme 3, reaction of 1,2,3,3,-tetramethyl-indolenine (1) with 1.2 equivalents of malonaldehyde dianil 6 in refluxing $Ac_2O$ (0.2 gm 1, 3 ml $Ac_2O$) for 1 hour yielded quantitatively crude solid acetanilide derivative 7 after cooling and precipitation with ether. The other reactive head group of the cyanine was formed by alkylation of methyl benzothiazole (8) with 5 equivalents of diiodopropane, diiodobutane, or diiodopentane in dry nitrobenzene overnight at 130–140° C. (5 gm diiodoalkane, 30 ml nitrobenzene). The derivatives were isolated as a pure solids after precipitation with ether to give the iodoalkyl derivatives 2 in 60–87% yield. The cyanine chromophore was then formed when compounds 2 and 7 were reacted with mild heating (heat to reflux then room temperature for 30 min) in the presence of 2 equivalents of triethylamine in dry EtOH (0.2 gms 2, 10 ml EtOH) to yield the iodoalkyl-TIN derivatives 9. The crude dye was precipitated with ether/petroleum ether and purified by flash chromatography eluting with $CH_2Cl_2$/methanol (20:1 v/v). Pure iodoalkyl-TIN 9 was recrystallized from $CH_2Cl_2$:methanol (10:1 v/v)/ether to give 60–90% yield of the dye as a dark blue powder.

Figure 5:
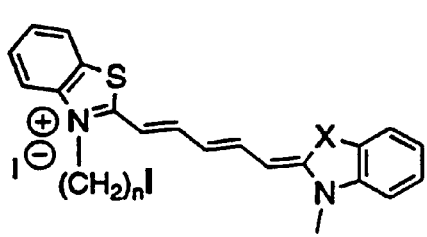
FIG. 5 is the formulae of the monomeric structures of the cyanine dyes used in the preparation of heterodimeric dyes of the subject invention.
Figure 5:
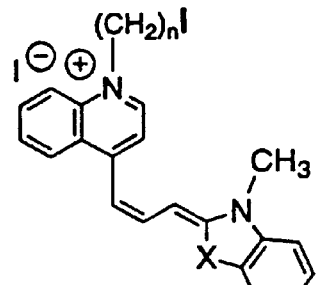
Figure 5:
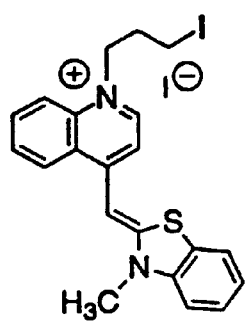
Figure 5:
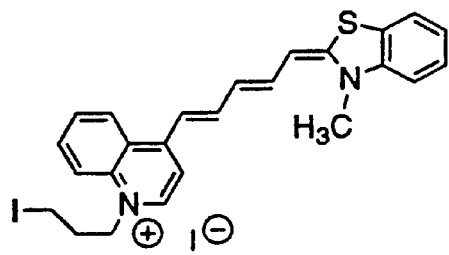
Figure 5:
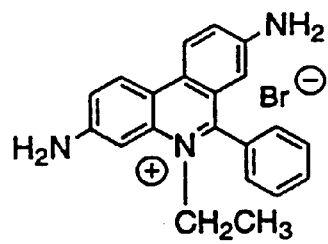

Similarly, the cyanine dyes 10–14, shown in FIG. 5, were synthesized from the appropriate derivatives in FIG. 4. The synthesis could be accomplished in either direction, starting with either activated quaternary heterocycle. Purified compounds gave single spots on TLC ($CH_2Cl_2$:methanol, 10:1 v/v) and their solutions in MeOH had distinctive absorbance spectra (Table 2) (Brooker et al. (1940) *J. Am. Chem. Soc.* 62, 1116–1125; Brooker et al. (1945) *Ibid.* 67, 1889–1893; Hammer F. M. (1964) *Chemistry of Heterocyclic Compounds*. Vol. 18, *The Cyanine and Related Compounds* (Weissberger, A.; Ed.), Interscience, New York; Benson & Kues (1977) *J. Chem. Engin. Data* 22, 379–383; West & Pearce (1965) *J. Phys. Chem.* 69, 1894–1903; Tyutyulkov et al. (1991) *Polymethine Dyes: Structure and properties*. St. Kliment Ohridski University Press, Sofia), with vibrant blue colors for dyes with absorption maxima above ~580 nm, and green for those with maxima above ~680 nm.

TABLE 2

Absorbance Maxima and Molar Extinction Coefficients of Monomeric Dyes

| Dye[a] | $\lambda^{Abs}_{max}$ (nm):$\epsilon(M^{-1}cm^{-1})$[b] | | |
|---|---|---|---|
| | MeOH | TAE | DNA |
| 9 (TIN) | 643: 230 200 | 639: 172 800 | 651: 142 600 |
| 10 (TAB) | 633: 160 500 | 628: 64 400 | 639: 61 200 |
| 11 (STAB) | 654: 189 500 | 649: 108 600 | 659: 44 100 |
| | | 586: 49 300 | 598: 43 600 |
| 13 (TO) | 506: 77 000 | 505: 52 700 | 512: 46 900 |
| 14 (TAG) | 732: 113 400 | 725: 35 500 | 739: 19 700 |
| | | 640: 31 400 | 657: 21 500 |
| 15 (EthBr) | 520: 5 200 | 475: 5 500[c] | 516: 3 700 |

[a]Average of 3 determinations for 9–11.
[b]All spectra were determined at room temperrture at a dye concentration of 3 × $10^{-6}$ M. TAE refers to 4 mM TAE buffer, pH 8.2. Calf thymus DNA at 20 bp:dye (6 × $10^{-5}$ M bp) was used for spectra of dsDNA-dye complexes in 4 mM TAE buffer pH 8.2. Spectra were measured after 15 min incubation.
[c]Literature value.

[a] Average of 3 determinations for 9–11.
[b] All spectra were determined at room temperature at a dye concentration of 3×$10^{-6}$ M. TAE refers to 4 mM TAE buffer, pH 8.2. Calf thymus DNA at 20 bp:dye (6×$10^{-5}$ M bp) was used for spectra of dsDNA-dye complexes in 4 mM TAE buffer pH 8.2. Spectra were measured after 15 min incubation.
[c] Literature value.

Synthesis of heterodimers

Figure 11:
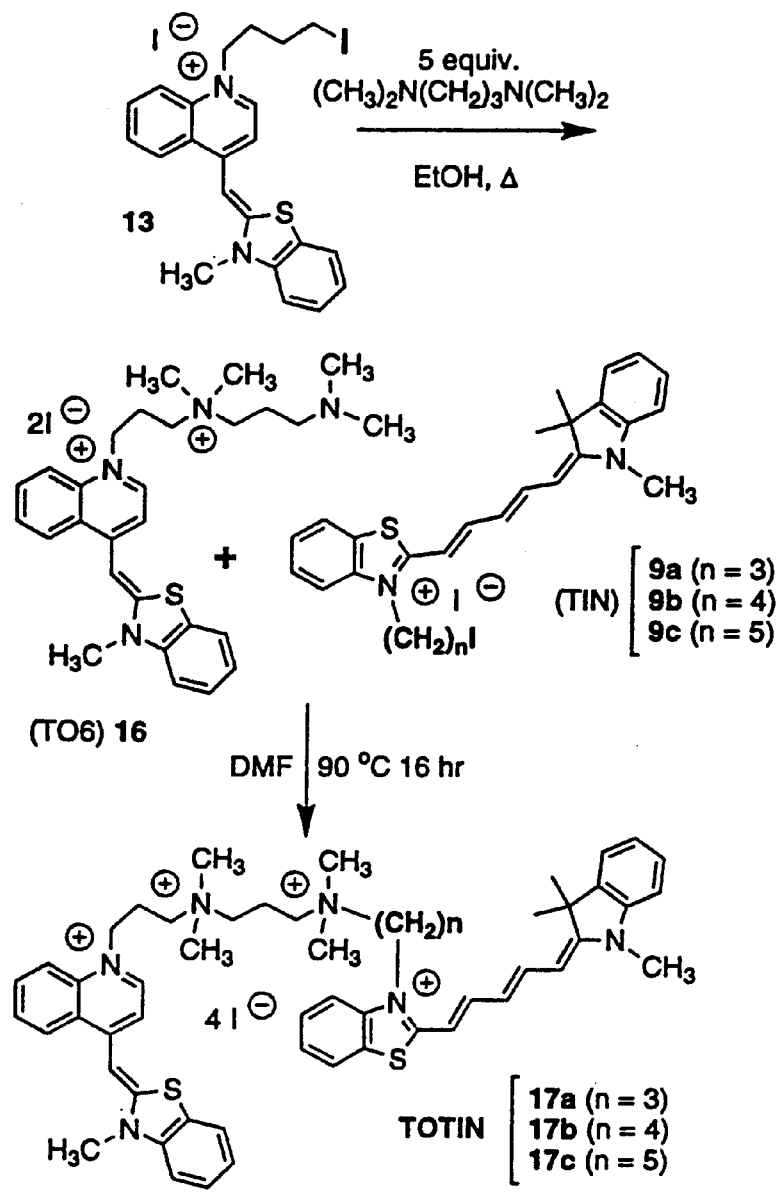
FIG. 11 (Scheme 4) is a flow chart for the synthesis of heterodimeric dyes (TOTIN) according to the subject invention.

In a manner similar to previously described syntheses, the synthesis of heterodimeric dyes followed the general procedure outlined in Scheme 4 (FIG. 11) for synthesis of the TOTIN heterodimers 17a–17c. The thiazole orange iodopropyl derivative (Benson et al. (1993) *Nucleic Acids Res.* 21, 5727–5735) reacted with 5 equivalents of N,N'-tetramethyldiaminopropane in refluxing ethanol for 6 hr to yield (tetramethylpropanediamino)propyl thiazole orange (TO6) (16, Benson et al. (1993) supra) quantitatively after precipitation with ether and recrystallization from $CH_2Cl_2$:MeOH (9:1)/ether. The reaction of TO6 and 1.5 equivalents of iodoalkyl-TIN 9 in anhydrous DMF (100 mg 9, 250 ul DMF) for 16–24 hours at 90° C. yielded crude dye after precipitation from the reaction mixture with ether/petroleum ether. Purification by flash chromatography employed gradient elution initially with EtOAc: AcOH: $H_2O$ (6:3:2, v/v) and finally EtOAc: AcOH: $H_2O$ (1:2:2, v/v) saturated with NaCl to elute the product dimer which runs slightly slower than unreacted diamino monomer on TLC in EtOAc: AcOH: $H_2O$ (1:2:2, v/v). Impure fractions from the first column were subjected to a final purification by reverse phase (Sephadex LH-20; Pharmacia) chromatography with $H_2O$/MeOH. After trituration of the dye/salt mixture with $CH_2Cl_2$:methanol, (10:1) to remove excess NaCl, the pure heterodimer product was precipitated with ether to give 17a–17c in 50–75% yield (moles of dye in a weighed sample determined from absorption spectrum in MeOH at 507 nm). No monomeric starting material was detected in the purified heterodimers by TLC in EtOAc:AcOH:$H_2O$ (1:2:2 v/v) or methanol:$CH_2Cl_2$ (1:10 v/v). The heterodimers 18–20 (FIG. 6) were synthesized by the same procedure.

Characterization of the dimers by $^1$H-NMR and mass spectrometry

Proton nuclear magnetic resonance spectra were recorded on a Bruker AMX-500 NMR spectrometer. The spectra were run in DMSO-$d_6$ and the chemical shifts were reported in parts per million (ppm) relative to the residual proton resonance at 2.49 ppm.

Electrospray ionization mass spectra (ESMS) were obtained on a VG Bio-Q electrospray triple quadrupole mass spectrometer in positive ionization mode with a skimmer voltage of 20–70 electron volts (eV). The electrospray mass spectrum (skimmer voltage=40 eV) of the heterodimers had major fragment peaks resulting from cleavage of the tetramethylpropanediamino linker to produce intact donor and acceptor fragments containing singly charged cations with dimethylaminoalkyl side chains. For example the mass spectrum of TOTIN 17a contained dimethylaminopropyl-TO ($C_{23}H_{26}N_3S^+$=376) and dimethylaminopropyl-TIN ($C_{28}H_{34}N_3S^+$=444). Similarly for the TOTAB and TOSTAB, the mass spectra had major fragment peaks corresponding to the cleavage fragments dimethylaminopropyl-TO and dimethylaminoalkyl-TAB or dimethylaminoalkyl-STAB, respectively.

Dissociation Rates of dsDNA-Dye Complexes during Agarose Gel Electrophoresis

The $t_{0.5}$ values for the dissociation of dsDNA-dye complexes, preformed at 20 bp:dye, were determined as described by Benson et al. (1993) *Nucleic Acids Res.* 21, 5720–5726.

RESULTS AND DISCUSSION

Absorption and Emission Spectra of the Monomers

The reactive intermediates of the dyes TIN (9), TAB (10), STAB (11), and TAG (14), were characterized spectroscopically (Tables 2 and 3), and then used for the synthesis of heterodimers.

TABLE 3

Fluorescence Emission Properties of Monomeric Dyes

| Dye | $\lambda^{Em}_{max}$ free: bound[a] (nm) | Enhancement bound/free |
|---|---|---|
| 9 (TIN) | 660: 670 | 1.8 |
| 10 (TAB) | 650: 658 | 388 |
| 11 (STAB) | 665: 675 | 2.5 |
| 13 (TO) | 538: 527 | 2600 |
| 14 (TAG) | 752: 758 | 35 |
| 15 (EthBr) | 610: 600 | 13 |

[a]All spectra were determined at 5 × $10^{-7}$ M dye at room temperature in 4 mM TAE buffer, pH 8.2. Calf thymus DNA at 100 bp:dye (6 × $10^{-5}$ M bp) was used for spectra of dsDNA-dye complexes in 4 mM TAE buffer pH 8.2. Spectra were measured after 15 min incubation. The fluorescence emission values were normalized to equal absorption at the $\lambda_{exc}$. Some residual unbound dye may be present under these conditions, consequently, the indicated ratios of relative fluoresence intensities of bound/free dye are approximate.

a All spectra were determined at 5×10-7 M dye at room temperature in 4 mM TAE buffer, pH 8.2. Calf thymus DNA at 100 bp:dye (6×10-5 M bp) was used for spectra of dsDNA-dye complexes in 4 mM TAE buffer pH 8.2. Spectra were measured after 15 min incubation at the $\lambda_{exc}$. Some residual unbound dye may be present under these conditions, consequently, the indicated ratios of relative fluoresence intensities of bound/free dye are approximate.

Absorption Spectra of the Heterodimers

The synthetic route to the heterodimers (Scheme 4) is similar to that we have previously described for the synthesis of TOTAB (propyl-TOTAB) Benson et al., (1993) supra. The TOTIN (17a–c), TOTAB (18a–d), TOSTAB (19), and TOTAG (20) were synthesized in this manner (Scheme 4 and FIG. 4). The length of the linker joining the donor and acceptor chromophores was varied systematically in the TOTIN and TOTAB heterodimer series.

The purified heterodimers contained traces of salt which were not easily removed and which precluded the determination of their absolute extinction coefficients by weight. Extinction coefficients of the heterodimers in methanol were calculated by addition of the extinction coefficients of the two monomers run at equal concentrations. The spectrum generated in this manner for a 1:1 molar mixture of the monomers matched closely the shape of the spectrum of the corresponding heterodimer. The extinction coefficients of the heterodimers 17–20 at 506 nm were determined from the known extinction coefficient of TO6 (16), and the extinction coefficients of 9–11 and 14 (all in methanol) established in this study.

From these data, we were able to determine the extinction coefficients of the heterodimers in TAE buffer and when bound to dsDNA in this buffer. At the short wavelength maximum (514–516 nm), due primarily to the thiazole orange chromophore, all of the dsDNA-bound heterodimers show similar extinction coefficients, 56,000–77,000 $M^{-1}cm^{-1}$ (Table 4).

TABLE 4

Absorbance Maxima and Molar Extinction Coefficients of Heterodimeric Dyes

| Dye[a] | $\lambda^{Abs}_{max}$ (nm):ε($M^{-1}cm^{-1}$)[b] | | |
|---|---|---|---|
| | MeOH | TAE | DNA |
| TOTIN | | | |
| 17a | 506: 79 000 | 508: 69 600 | 515: 60 000 |
| | 647: 146 400 | 649: 126 500 | 653: 102 300 |
| 17b | 507: 79 000 | 507: 75 700 | 515: 66 700 |
| | 643: 152 000 | 649: 114 000 | 651: 111 000 |
| 17c | 507: 79 000 | 507: 75 000 | 515: 62 100 |
| | 643: 154 000 | 649: 107 000 | 650: 110 000 |
| TOTAB | | | |
| 18a | 507: 77 600 | 506: 74 300 | 514: 59 800 |
| | 636: 101 000 | 645: 79 700 | 646: 50 000 |
| 18b | 507: 77 600 | 505: 72 600 | 515: 58 500 |
| | 634: 101 000 | 644: 66 600 | 633: 30 400 |
| 18c | 507: 77 600 | 503: 72 900 | 514: 56 000 |
| | 634: 101 000 | 649: 49 000 | 640: 37 000 |
| 18d | 507: 77 600 | 502: 61 500 | 516: 62 500 |
| | 632: 116 000 | 649: 40 400 | 633: 49 100 |
| TOSTAB | | | |
| 19 | 507: 77 600 | 509: 77 200 | 515: 76 700 |
| | 654: 149 000 | 657: 131 000 | 656: 99 400 |
| TOTAG | | | |
| 20 | 506: 77 600 | 507: 51 700 | 514: 56 400 |
| | 738: 69 800 | 748: 37 400 | 751: 29 700 |

[a] All spectra were determined at room temperature at a dye concentration of 3×10³¹ ⁶ M. TAE refers to 4 mM TAE buffer, pH 8.2. Calf thymus DNA at 20 bp:dye (6×$10^{-5}$ M bp was used for spectra of dsDNA-dye complexes in 4 mM TAE buffer pH 8.2. Spectra were measured after 15 min incubation.

Fluorescence Emission Spectra of the dsDNA-Bound Heterodimers

Figure 7:
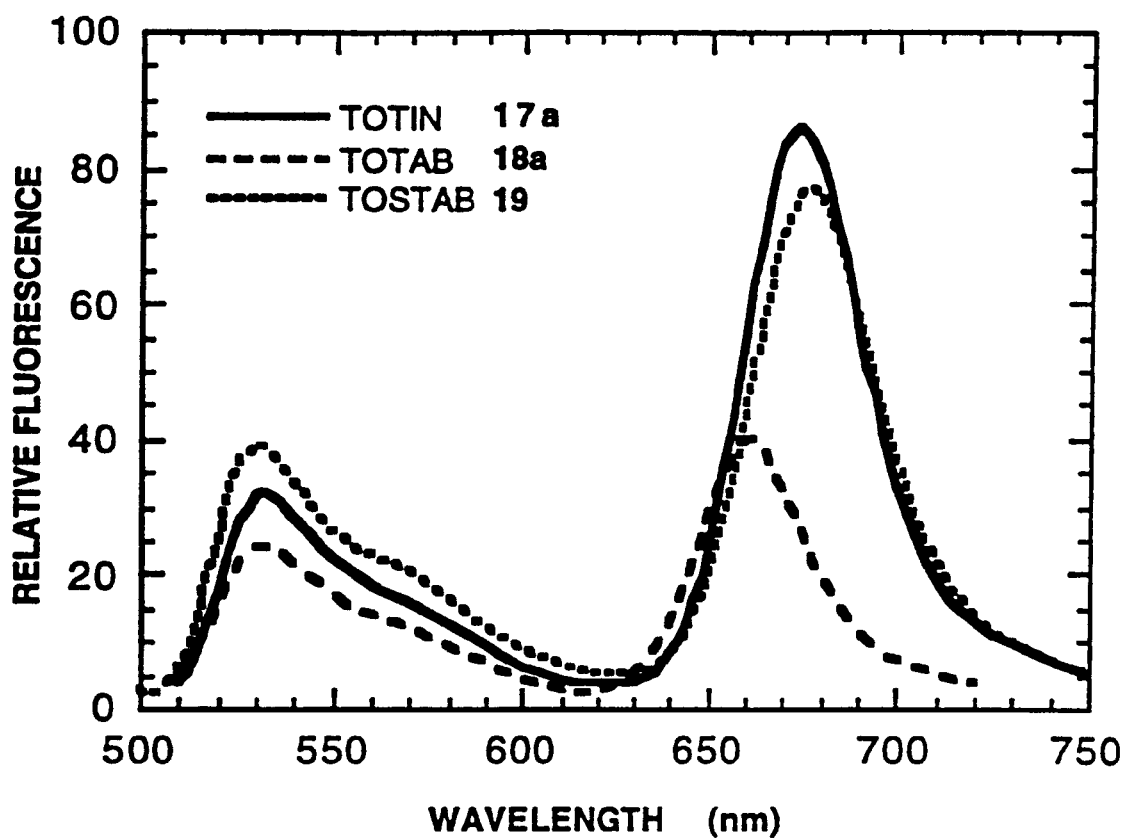
FIG. 7 is a graph of the fluorescence emission spectra for 488 nm excitation of TOTIN 17a, TOTAB 18a, and TOSTAB 19 bound to dsDNA. The dyes ($5\times 10^{-7}$M) were added to calf thymus DNA ($5\times10^{-5}$M bp) in 4 mM TAE, pH 8.2, at 1 dye: 100 bp. Spectra were recorded after incubation of the mixtures for 15 min in the dark.
Figure 8:
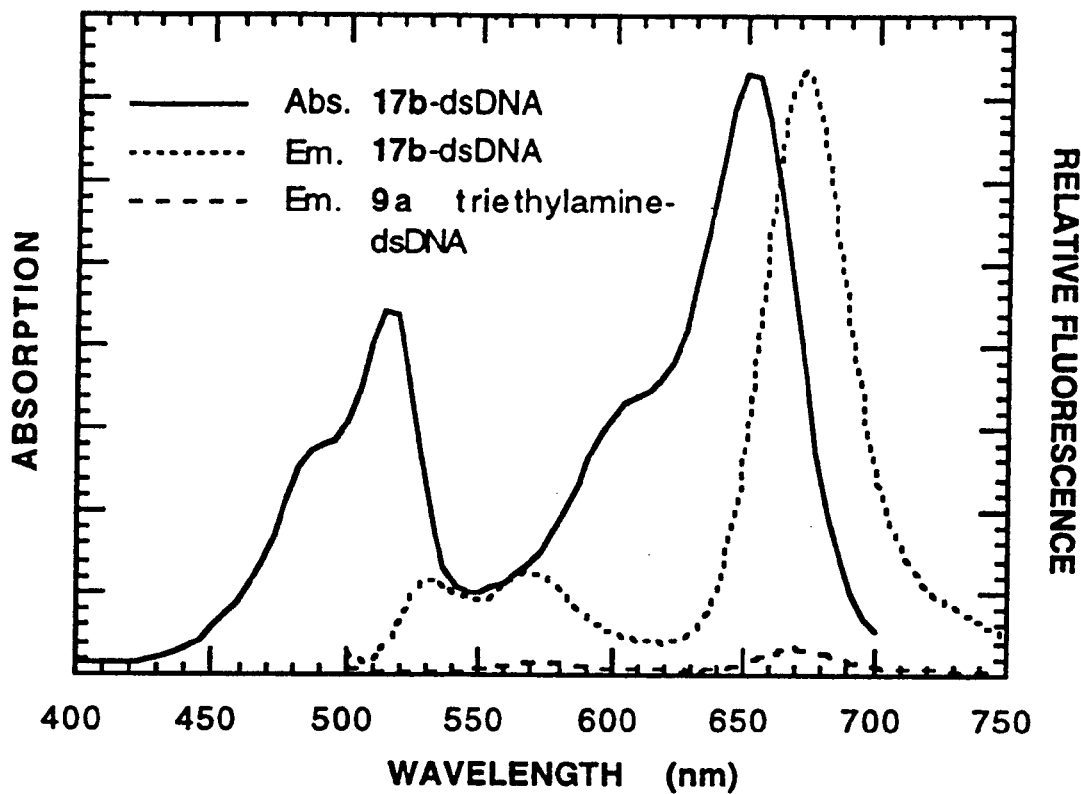
FIG. 8 is a graph of the absorbance and emission spectra of the dsDNA-TOTIN 17b complex. The solid curve corresponds to the absorbance spectrum of dye ($3\times^{-6}$M) added to calf thymus DNA ( $6\times10^{-5}$M bp) at 1 dye:20 bp in 4 mM TAE buffer, pH 8.2. The two dashed curves compare the relative emissions of the TOTIN 17b and of the TIN 10a triethylammonium derivative in the presence of dsDNA for excitation at 488 nm. The upper dashed curve represents the fluorescence emission spectrum of TOTIN 17b ($5\times10^{-7}$M) added to calf thymus DNA ( $5\times10^{-5}$M bp) at 1 dye:100 bp in 4 mM TAE, pH 8.2, and the lower dashed curve corresponds to fluorescence emission of a solution of the TIN 9a triethylammonium derivative with the same absorbance at 649 nm as the TOTIN 17b solution used for the preceding fluorescence emission spectrum determination and added to the same amount of dsDNA.
Figure 9:
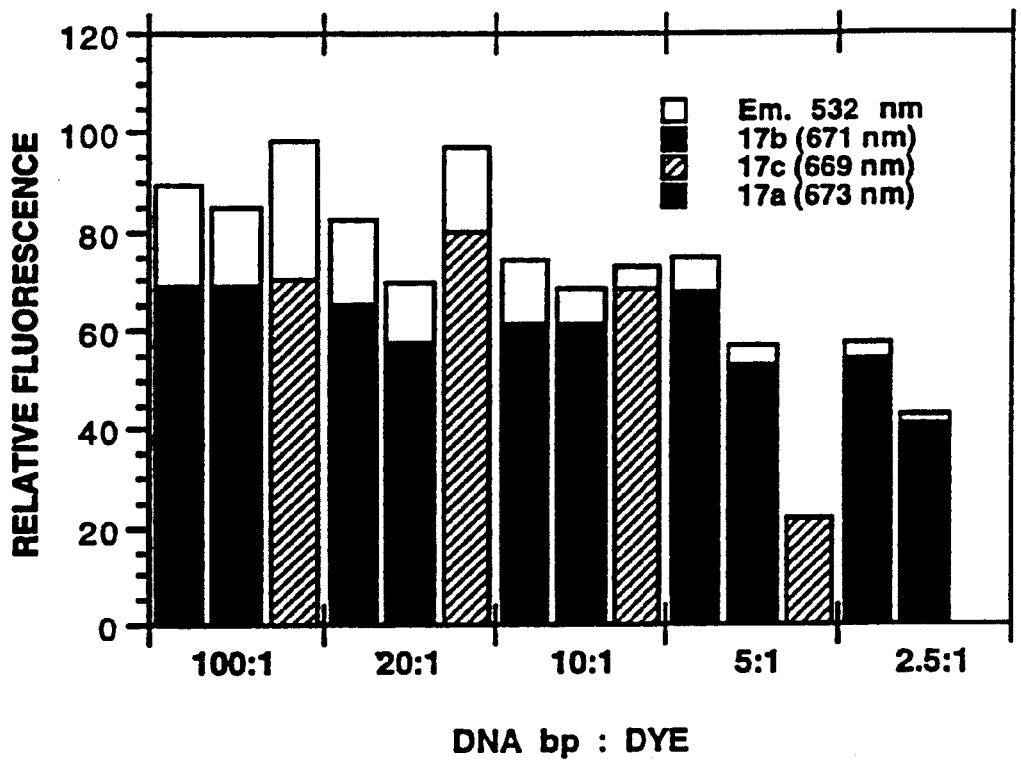
FIG. 9 is a bar graph of the fluorescence emission characteristics of TOTIN 17a–c ($5\times10^{-7}$M) mixed with calf thymus DNA in a 4 mM TAE buffer, pH 8.2 at dye:DNA bp ratios ranging from 1:100 to 1:2.5. Excitation was at 488 nm. Emission intensities were recorded after 15 min incubation in the dark at the $\lambda^{Em}_{max}$ of TIN at 669 to 673 nm and of TO at 532 nm.

To compare energy transfer efficiency and relative emission intensities of the heterodimers, the dyes were mixed with dsDNA at a ratio of 1 dye molecule per 100 bp. The emission spectra for 488 nm excitation were then measured (FIG. 7). The extent of quenching of the thiazole orange (donor) chromophore was determined by comparing the emission spectra obtained for solutions of equal 488 nm absorbance of the dsDNA-bound heterodimers and that of dsDNA-bound thiazole orange monomer, TO6 (16). The thiazole orange emission ($\lambda_{max}$ 532 nm) was quenched by 83% or more in the TOTIN, TOTAB, and TOSTAB heterodimers (Table 5). In spite of the fact that the quenching of the donor emission is most efficient in the TOTAB dyes, the higher molar extinction coefficients of the TIN and STAB chromophores (Table 4) result in heterodimers with twice as high acceptor fluorescence emissions (Table 5). Energy transfer efficiency in the dsDNA-TOTAG (20) complex was poor. Donor emission was quenched by only 65%. Moreover, the low fluorescence quantum yield of the acceptor, TAG (14), resulted in a ratio of donor:acceptor fluorescence emission ratio of 44:1. On the basis of these results, the TOTAG heterodimer was of lesser interest than the other dyes.

TABLE 5

Characteristics of the Fluorescence Emission Spectra of Heterodimeric Dyes Complexed with dsDNA.

| Dye | $\lambda^{Em}_{max}$[a] donor: acceptor (nm) | Ratio[b] donor: acceptor | Rel. Fluor.[c] | Donor Quenching (%) | Enhancement bound/free | $t_{0.5}$[d] (min) |
|---|---|---|---|---|---|---|
| TOTIN | | | | | | |
| 17a | 531: 673 | 1:3.5 | 2.1 | 88% | 36 | 112 |
| 17b | 530: 671 | 1:4.3 | 2.1 | 90 | | 317 |
| 17c | 530: 669 | 1:2.5 | 2.1 | 83 | | 129 |
| TOTAB | | | | | | |
| 18a | 532: 658 | 1:1.2 | 1 | 91 | 126 | 131 |
| 18b | 530: 655 | 1:1 | 0.76 | 92 | | 242 |
| 18c | 531: 658 | 1:1.6 | 1 | 93 | | 1300 |
| 18d | 531: 654 | 1:0.6 | 0.44 | 92 | | 105 |
| TOSTAB | | | | | | |
| 19 | 530: 677 | 1:2.4 | 1.9 | 85 | 80 | 63 |

[a]All spectra were determined at 5 × 10$^{-7}$ M dye at room temperture in 4 mM TAE buffer, pH 8.2. From spectra of calf thymus DNA ds DNA-dye complexes at 100 bp:dye (6 × 10$^{-5}$ M bp) in 4 mM TAE buffer pH 8.2. Spectra were measured after 15 min incubation.
[b]Ratio of fluorescence emission intensities at $\lambda^{Em}_{max}$ of donor and acceptor.
[c]Acceptor emission intensity normalized per mole to $\lambda^{Em}_{max\ of\ TOTAB\ 18a\ at\ 658\ nm}$.
[d]Calculated from first order rate of loss of dye during electrophoresis determined by assay described in Benson et al. (1993) Nucleic Acids Research 21, 5720–5728.

a All spectra were determined at 5×10$^{-7}$ M dye at room temperature in 4 mM TAE buffer, pH 8.2. From spectra of calf thymus DNA ds DNA-dye complexes at 100 bp:dye (6×10–5 M bp) in 4 nM TAE buffer pH 8.2. Spectra were measured after 15 min incubation.
b Ratio of fluorescence emission intensities at $\lambda^{Em}_{max}$ of donor and acceptor.
c Acceptor emission intensity normalized per mole to $\lambda^{Em}_{max}$ of TOTAB 18aat 658 nm.
d Calculator from first order rate of loss of dye during electrophoresis determined by assay described in Benson et al. (1993) Nucleic Acids Research 21, 5720–5728.

Energy transfer in the heterodimers leads to impressive gains in long wavelength emission for 488 nm excitation relative to direct excitation of an equal concentration of the monomer acceptor chromophore. FIG. 5 compares the emission spectra of dsDNA-bound TIN derivative 9b (Scheme 2) with that of the dsDNA-TOTIN complex (18b). The long-wavelength emission of the heterodimer is almost 25-fold higher than that of the monomer. Most of the enhanced emission of the heterodimer can be attributed to the much greater absorption cross-section at $\lambda_{exc}$ (488nm) of TOTIN versus TIN contributed by the TO moiety.

Effect of Linker Length on Enuission Spectra of dsDNA bound Heterodimers

Figure 6:
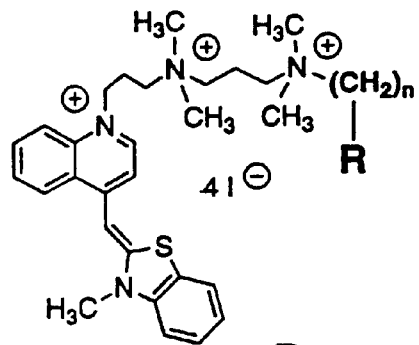
FIG. 6 is the formulae of the heterodimeric structures of dyes according to the subject invention.
Figure 6:
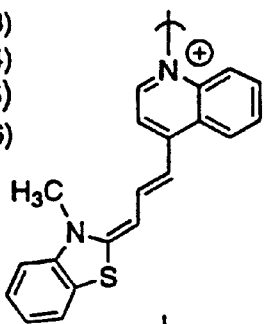
Figure 6:
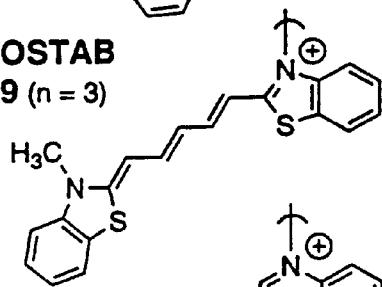
Figure 6:
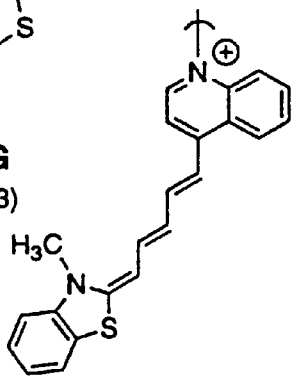

In the TOTIN 17a–c and TOTAB 18a–d heterodimers, there is a stepwise increase within each series of the length of the bridge between the donor and acceptor by one —CH$_2$— group (Scheme 4; FIG. 6). The fluorescence emission spectra of these heterodimers were determined at a fixed concentration of dye at a dye:DNA bp ratio of 1:100. For both types of heterodimers, the linker length strongly affected the ratio and intensity of the emission of the dsDNA-bound dyes. From the data presented in Table 5, it is evident that energy transfer was optimized in 17b (butyl TOTIN), presumably because of a more favorable geometry for energy transfer of the donor and acceptor chromophores. The fluorescence emission intensity is the same for 17a–c, most likely because the magnitude of the emission is dominated by the fluorescence quantum yield of the acceptor. In contrast, the emission spectra of dsDNA-bound TOTAB derivatives 18a–d showed unchanged extent of energy transfer (~92%), but large variations in the relative fluorescence emission of the acceptor. TAB emission was quenched in the butyl 18b and hexyl 18d relative to the propyl 18a and pentyl 18c derivatives (Table 5). The variations in TAB quenching correlated with changes in the emission maxima (655 nm and 658 nm) and hypochromicity of the TAB absorption (Table 4). The sensitivity of the emission and absorption spectrum of TOTAB to linker length suggests that the degree of intercalative binding of TOTAB is strongly dependent on the exact linker length.

Titration of TOTIN Heterodimers with DNA

TOTIN derivatives 17a–c were titrated with calf thymus DNA at a fixed dye concentration to determine the effect of the degree of saturation of binding sites on the fluorescence emission intensity per mole of bound dye. FIG. 7 illustrates the titration of 17a (propyl TOTIN). The TIN emission at 672 nm is seen to be nearly constant for dye:bp DNA ratios from 1:100 to 1:5. Similar results were obtained for 17b (butyl TOTIN) up to a dye:bp DNA ratio of 1:10 and 17c (pentyl TOTIN) up to 1:20. At higher dye:bp DNA ratios, there is a significant drop-off in fluorescence emission intensity per mole of dye. These results suggest that for the TOTIN derivatives, the fluorescence intensity per mole of bound dye is essentially constant as long as binding sites are available and that are no significant dye-dye quenching interactions. The comparative data on the ratio dependence of the emissions of 17a–c suggests that the size of the binding site increases significantly with increase in the length of the linker. The low of sensitivity of fluorescence intensity to the degree of binding site saturation makes TOTIN a good candidate for use in multiplex quantitation experiments.

Stability of Dye/DNA Complexes during Gel Electrophoresis

The rate of dissociation of dye-DNA complexes during electrophoresis offers a valuable measure of the relative usefulness of different fluorescent ligands as labels for multiplex detection of DNA in various formats. The electrophoretic off-rate assay was used to assay the homologous series of TOTIN and TOTAB heterodimers. The assay was performed on pre-formed complexes of TOTIN 17a–c and TOTAB 18a–d with λDNA/Hind III restriction fragments to determine the $t_{0.5}$ for loss of the dye during electrophoresis. The data in Table 5 show that for heterodimers with particular linker lengths, the stability of the dsDNA complexes is greatly enhanced over that for homologous molecules with either shorter or longer linker. For TOTIN, the optimum $t_{0.5}$, 317 min, is seen for 17b, where n=4 (Scheme 2). For TOTAB 18c, where n=5 (FIG. 6), the maximum $t_{0.5}$ of 1300 min is ten-fold longer than that for 18a, where n=3, and twelve-fold higher than for 18d, where n=6. The stability of the TOTAB 18c dsDNA complex to electrophoresis is the highest yet reported for a heterodimeric dye. These data suggest strongly that modest changes in the linker length make a significant difference to the amount of deformation of dsDNA conformation that accompanies heterodimeric polycationic dye binding, and, in this manner, to the stability of the complex.

EXAMPLE 3

Detection of dsDNA Fragments with TOTIN & TOTAB Heterodimers

MATERIALS AND METHODS

One kb ladder was obtained from GIBCO BRL (Life Technologies, Inc., Gaithersburg, Md.) and λDNA/HindIII from Sigma (St. Louis, Mo.). Stock doublestranded DNA (dsDNA) solutions were stored at −20° C. Concentrated stock solutions of dyes ($10^{-4}$ M in methanol or DMSO) were stored at −20° C. Freshly diluted dye solutions ($10^{-6}$ M) were prepared in 4 mM TAE, pH 8.2, immediately before use.

The following exemplifies the procedure for the preparation of dye/DNA complexes in advance of electrophoresis. For a final concentration of 0.2 ng DNA per $\mu$l, stock DNA (10 ng/$\mu$l; 2 ml) was added to an appropriately diluted dye solution in 4 mM TAE-50 mM NaCl, pH 8.2, to give a total of 75 $\mu$l. The mixture was incubated in the dark for 30 min, and then 25 $\mu$l of 15% (w/v) aqueous Ficoll was added. Five $\mu$l aliquots of the final mixture were then loaded with a 20 $\mu$l syringe to give 1 ng loads. Where desired, the DNA load was varied by changing the concentration in the incubation mixture. For two-color experiments, 50 $\mu$l of two separate Ficoll-containing samples were mixed together by re-pipeting 4 times.

Electrophoresis was performed on vertical agarose gels (Ultrapure™ agarose, Bethesda Research Laboratories), 1 mm thick, 0.9% agarose in 40 mM TAE, pH 8.2, in a Bio-Rad (Richmond, Calif.) Mini-Protean II apparatus. The gels were subjected to pre-electrophoresis for 1 hr prior to sample loading. Samples were electrophoresed at 10 V/cm. For the determination of off-rates, equal aliquots of a dye-DNA mixture were loaded into consecutive wells on a gel at appropriate time intervals (typically every 15 min.) to allow determination of the integrated fluorescence intensity of a given band as a function of the length of time of electrophoresis. For post-staining, the gel sandwich was carefully removed from between the plates while these were submerged in buffer (100 ml). A concentrated aliquot of dye was added to the buffer to a final concentration of $\sim 1 \times 10^{-7}$ M. After gentle agitation for 30 min, the gel was transferred to fresh buffer and agitated for 20 min. The gel sandwich including the spacers was reassembled for scanning while submerged to eliminate trapped bubbles.

Gels were scanned with a two-color confocal laser excited fluorescence imaging system, (Mathies et al., (1994) *Rev. Sci. Instrum.* 65, 807–812). The complete gel sandwich with spacers was dried and taped to the scan stage. The filters used for the detection of TOTO and TOTAB complexes were those described in Zhu et al. (1994) *Anal. Chem.* 66, 1941–1948. For 647 nm excitation of the TIN chromophore, a 647 nm notch filter was placed in front of the laser to reduce plasma fluorescence and a 647 nm rejection filter was placed in front of the detector to exclude reflected laser light. After scanning (10 min; 6 cm×6 cm), the data were transformed into Mac Image™ files to produce pseudo images and transformed into ScanAnalysis™ (BioSoft, Cambridge, UK) files to determine the integrated fluorescence intensity of the bands, as described in Mathies et al. (1994) supra and Rye et al (1995) *Nucleic Acids Res.* 23, 1215–1222.

RESULTS AND DISCUSSION

Two-color Multiplex Separations

Figure 12:
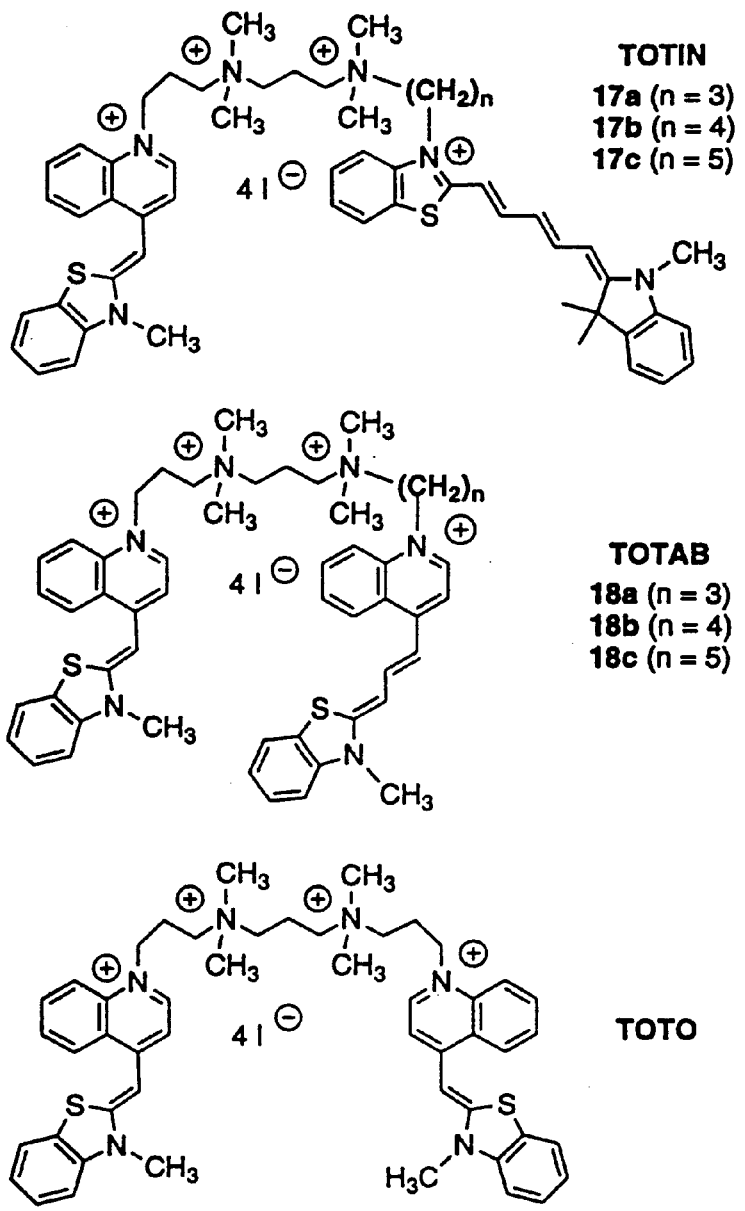
FIG. 12 provides the strutures of thiazole orange-thiazole indolenine heterodimers (TOTIN 17a–c), thiazole orange-thiazole blue heterodimers (TOTAB 18a–c), and thiazole orange homodimer (TOTO).

The structures of the dyes used in these experiments are shown in FIG. 12.

Previous two-color restriction fragment mapping experiments with TOTAB 18a and TOTO showed that there was little migration of dye between from one pre-labeled complex to the other and that the binding of either dye led to a similar amount of systematic retardation of dsDNA fragments. It was anticipated that the more stable complexes with the new TOTAB dyes, 18b and 18c, would offer advantages over those with 18a. For the TOTIN dyes 17a–c, the higher acceptor fluorescence emission intensity was also expected to be advantageous.

Figure 13:
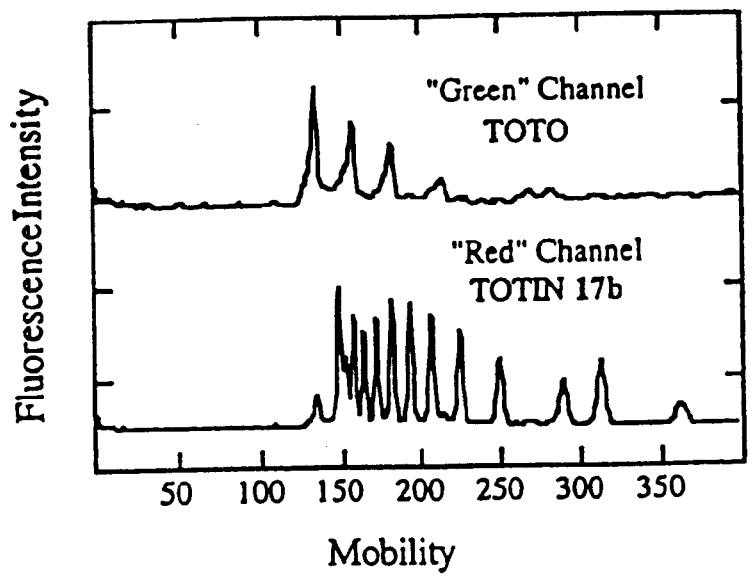
FIG. 13A shows the densitometric fluorescence intensity plots for lanes of an agarose gel with 5 ng 1 kb ladder DNA-TOTIN 17b complex mixed with 3 ng λDNA/HindIII-TOTO complex after 60 min electrophoresis.
FIG. 13B shows a least squares plot of the mobilities of complexes of λDNA/HindIII-TOTO (filled circles), determined from the date in FIG. 13A, against 1/ln (fragment size). The data points for the mobilities of 1 kb ladder DNA-TOTIN 17b complexes (empty squares) were used to calculate the sizes of these fragments.
Figure 13:
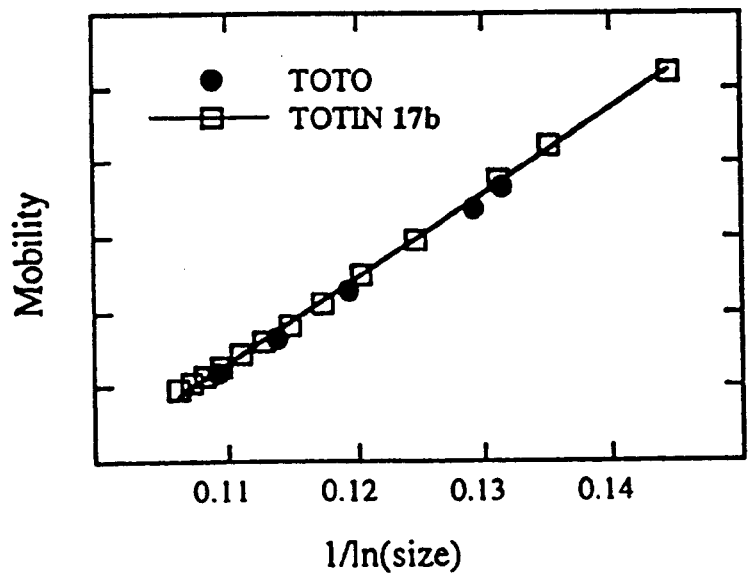

For the sizing experiments, a 1 kb ladder was complexed with an energy transfer heterodimer dye to serve as a calibration standard and a second ladder, λDNA/HindIII, was complexed with TOTO. At a dsDNA bp:dye ratio of 20:1 or higher, the rate of dye loss for all complexes followed apparent first order kinetics. TOTO-DNA complexes were detected in the "green channel" (500–565 nm), while complexes with the energy transfer dyes were detected in the "red channel" (645–750 nm). Little crosstalk of the emissions was observed. TOTIN 17b and TOTAB 18c gave the best results with the least migration of dyes between two sets of DNA-dye complexes (FIG. 13A). As shown in FIG. 13A, none of the DNA fragments labeled with TOTIN are detectable in the green channel; the only TOTO-labeled fragment detectable in the red channel is the 23 kbp fragment which shows up as a weak peak.

Mobility shifts of DNA-dye complexes

Multiplex sizing of dsDNA fragments requires information about the mobility shift induced by binding of each of the dyes. To obtain this information, 1 kb ladders labeled with each of the dyes TOTAB 18a–c and TOTIN 17a–c were used as standards to size TOTO-labeled λDNA/HindIII fragments.

Linear plots of mobility versus 1/ln(fragment size) with very high correlation coefficients were obtained for each set of dsDNA-dye complexes indicating that the dyes did not exhibit significant sequence specificity (for example, see FIG. 13B). The standard curves allowed precise determination of the apparent sizes of the λDNA/HindIII fragments. The sizes are termed "apparent" because the determination does not take into account differences in mobility shifts between the dsDNA complexes with these pairs of dyes.

An estimate of the difference in mobility shift is given by the difference between the measured and actual sizes of the λDNA/HindIII fragments. The relevant data are compiled in Table 6.

TABLE 6

Comparison of the calculated and actual sizes of λDNA/HindIII fragments determined from sizing of the TOTO complexes with 1 kb ladder complexes with various TOTIN and TOTAB dyes as internal standards.[a]

| Fragment size (bp) | Calculated size (% Error ± standard deviation)[b] | | |
|---|---|---|---|
| | TOTAB 24a | TOTAB 24b | TOTAB 24c |
| 9416 | 9516 (−1.6) | 8796 (−6.6) | 8643 (−8.2) |
| 6557 | 6811 (3.9) | 6587 (0.5) | 6362 (−3.0) |
| 4361 | 4478 (2.7) | 4556 (4.5) | 4479 (2.7) |
| 2322 | 2394 (3.1) | 2374 (2.2) | 2367 (1.9) |
| 2027 | 2046 (0.9) | 2075 (2.4) | 2069 (2.1) |
| Avg.b | 1.8 ± 6.4% | 2.2 ± 4.5% | 1.9 ± 4.7% |
| | TOTIN 23a | TOTIN 23b | TOTIN 23c |

TABLE 6-continued

Comparison of the calculated and actual sizes of λDNA/HindIII fragments determined from sizing of the TOTO complexes with 1 kb ladder complexes with various TOTIN and TOTAB dyes as internal standards.[a]

| Fragment size (bp) | Calculated size (% Error ± standard deviation)[b] | | |
| --- | --- | --- | --- |
| 9416 | 9025 (−4.1) | 9898 (5.1) | 9857 (4.7) |
| 6557 | 6981 (6.5) | 7020 (7.1) | 7011 (6.9) |
| 4361 | 4946 (13.4) | 4612 (5.8) | 4564 (4.7) |
| 2322 | 2515 (8.3) | 2442 (5.2) | 2406 (3.6) |
| 2027 | 2128 (5.0) | 2109 (4.0) | 2102 (3.7) |
| Avg. | 5.8 ± 6.4% | 5.2 ± 1.1% | 4.7 ± 1.3% |

[a]Dye: DNA bp ratio was 1:20
[b]Average of the error of each band and the standard deviation of the error.

[a] Dye: DNA bp ratio was 1:2.
[b] Average of the error of each band and the standard deviation of the error.

The data in Table 6 lead to several interesting observations. For a given series of homologous dyes (TOTAB 18a–c or TOTIN 17a–c), the mobility shift is unaffected by the stepwise change in the length of the linker. Surprisingly, the mobility shift is similar for dyes with similar linkers but very different chromophores. The maximum discrepancy between the actual and estimated fragment size is ~5%, between dsDNA-TOTO and dsDNA-TOTIN 17a–c complexes. For the TOTO/TOTIN multiplex sizing experiments, introduction of a systematic 5% adjustment to the mobility values for the TOTO-labeled fragments allows sizing with an error of less than 1.3%.

Dependence of the sensitivity of detection and quantitation of dsDNA-dye complexes on excitation wavelength The spectroscopic properties of the TOTAB and TOTIN dyes allow fluorescence detection of complexes with these dyes either by exciting the TO chromophore with the argon ion laser at 488 nm, or by exciting the TAB or TIN chromophores at 633 nm (He—Ne laser) or 647 nm (krypton laser). The "red" excitation is a useful option because He—Ne lasers are relatively inexpensive and autofluorescence contributions from biological materials to the emission above 600 nm are low.

Figure 14:
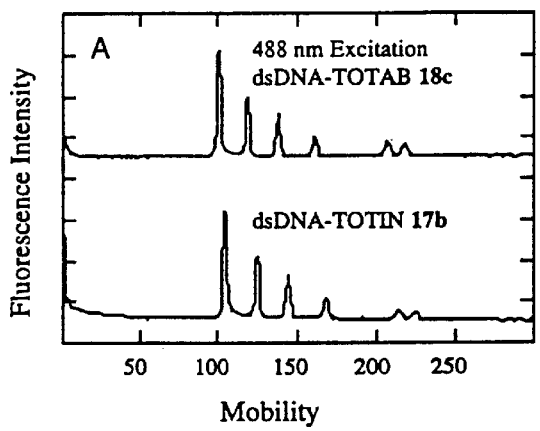
FIG. 14 provides a comparison of TOTAB 18c and TOTIN 17b-dsDNA complexes with excitation at 488 and at 647 nm. A & C show the densitometric fluorescence intensity plots for lanes of an agarose gel with 0.25 ng λDNA/HindIII-TOTAB 18c or λDNA/HindIII-TOTIN 17b, for excitation at 488 nm and 647 nm, respectively, after 60 min electrophoresis. B & D show the linear dependence of the fluorescence intensity on fragment size for 488 nm excitation (B) and 647 nm excitation (D). The amount of the smallest λDNA/HindIII fragment on the gel was ~10 pg.
Figure 14:
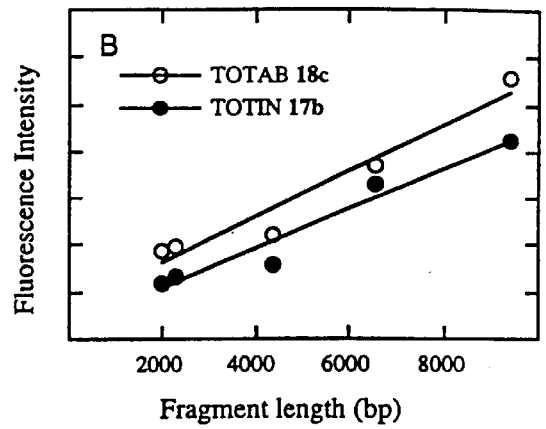
Figure 14:
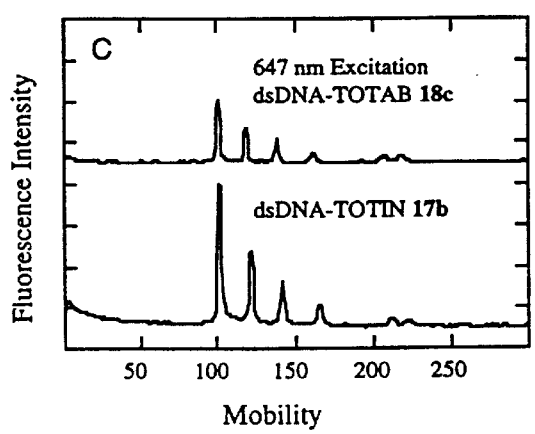
Figure 14:
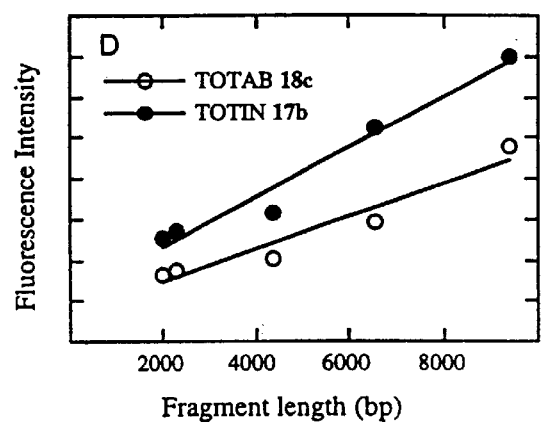

In FIG. 14, we compare the sensitivity of detection of λDNA/HindIII fragments labeled with either TOTAB 18c or TOTIN 17b and excited at either 488 and 647 nm. In this experiment, the window for the detection of fluorescence emission from each dye was the same for both excitation wavelengths. Similar quantitative results were obtained for excitation at the two wavelengths and the limit of detection of a dsDNA band (5×1 mm) was ~5 pg with either dye (FIG. 14).

It is evident from the above results, that the subject dyes provide a new chemical class of heterodimeric dsDNA-binding dyes which exploit energy transfer. The large Stokes shift and the red emission of the subject dyes are particularly favorable because they allow efficient rejection of extraneous fluorescence in Raman scattering of water. Such dyes are valuable for high sensitivity fluorescence detection of DNA, particularly in multiplex formats.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A kit comprising a plurality of dyes, wherein at least one of said dyes is heterodimeric and a combination of donor and acceptor chromophores selected from the group consisting of indolenine-benzoheteroazole, quinolinium-benzoheteroazole and benzoheteroazole-benzoheteroazole, wherein said hetero is oxygen, nitrogen or sulfur and said chromophores are linked by an alkyleneaminoalkylene linking group, wherein the length of one of said alkylene groups is different from the other alkylene groups and results in enhancing at least one of percent quenching of the donor chromophore and dsDNA affinity in gel electrophoresis, wherein said dsDNA affinity as measured by $t_{0.5}$ (min) in agarose gel electrophoresis is at least 150.

2. A kit according to claim 1, wherein said at least one of said dyes comprises an alkyleneaminoalkylene bridge having two amino groups and the alkylene bonded to one of said chromophores is of a different number of carbon atoms than the other alkylene groups.

3. A kit according to claim 1, wherein said heterodimeric dyes have the same donor chromophore.

4. A kit according to claim 3, wherein said donor chromophore is a benzothiazole-quinolinium dye.

5. A kit according to claim 4, wherein said benzothiazole-quinolinium dye is thiazole orange.

6. dsDNA to which is bound a heterodimeric dye selected from the group consisting of TOTIN-butyl having the structure of 17b of FIG. 12, TOTAB-butyl having the structure of 18b of FIG. 12 and TOTAB-pentyl having the structure of 18c of FIG. 12.

7. TOTIN-butyl having the structure of 17 b of FIG. 12.

8. TOTAB-butyl having the structure of 18b of FIG. 12.

9. TOTAB-pentyl having the structure of the 18c of FIG. 12.

10. In a method for separating components of a mixture using a plurality of dyes having different fluorescent emission wavelengths, the improvement which comprises:

using as one of said dyes, a dye selected from the group consisting of TOTIN-butyl having the structure of 17b of FIG. 12, TOTAB-butyl having the structure of the 18b of FIG. 12, and TOTAB-pentyl having the structure of 18c of FIG. 12.

* * * * *